(12) United States Patent
Kongsbak et al.

(10) Patent No.: US 6,461,610 B1
(45) Date of Patent: Oct. 8, 2002

(54) METHODS FOR MODIFYING CELL MOTILITY USING FACTOR VIIA OR INACTIVATED FACTOR VIIA

(75) Inventors: Lars Kongsbak, Holte; Niels Bergenhem, Frederiksberg C; Lars Christian Petersen, Hørsholm; Ole Thastrup, Birkerød, all of (DK); Don Foster, Seattle, WA (US); Mirella Ezban, Copenhagen ø (DK); Agneta Siegbahn, Uppsala (SE)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/372,888

(22) Filed: Aug. 12, 1999

Related U.S. Application Data

(63) Continuation-in-part of application No. 09/116,748, filed on Jul. 16, 1998, now Pat. No. 6,268,163.
(60) Provisional application No. 60/052,922, filed on Jul. 21, 1997.

(30) Foreign Application Priority Data

Jul. 18, 1997 (DK) .............................. 0879/97

(51) Int. Cl.[7] .............................. A61K 38/48
(52) U.S. Cl. .................. 424/94.64; 514/12; 514/2; 424/94.64
(58) Field of Search ..................... 514/2, 12; 424/94.64

(56) References Cited

U.S. PATENT DOCUMENTS 5,753,446 A    5/1998   Johnson

FOREIGN PATENT DOCUMENTS

| EP | 0 244 221 | 11/1987 |
| WO | WO 94/05328 | 3/1994 |
| WO | WO 96/12800 | 5/1996 |
| WO | WO 96/40276 | 12/1996 |
| WO | WO 97/22717 | 6/1997 |

OTHER PUBLICATIONS

Sato et al., "Tissue Factor Induces Migration of Cultured Aortic Smooth Muscle Cells" (1996) Thromb. Haemost. 75(3), 389–392.*
Sato et al., "Tissue Factor Pathway Inhibitor Aortic Smooth Muscle Cell Migration Induced by Tissue Factor/Factor VIIa Complex", Sep. 01, 1997, Thromb. Haemost. 78(3), pp. 1138–1141.*
Sato et al., "Tissue Factor Induces Migration of Cultured Aortic Smooth Muscle Cells", Aug. 1, 1996, Thromb. Haemost. 75(3), pp. 389–392, in EMBASE, AN 96104512.*
Versteeg et al., "Factor VIIa/Tissue Factor–induced Signalling via Activation of Src–like Kinases, Phosphatidylinositol 3–Kinase, and Rac", Sep. 15, 2000, J. Mol. Biol., 275(37), pp. 28750–28756.*
Sato et al., "Overexpression of Tissue Factor Pathway Inhibitor in Aortic Smooth Muscle Cells Inhibits Migration Induced by Tissue Factor/Factor VIIa Complex", Jun. 15, 1999, Thromb. Res., 94(6), pp. 401–406.*
Ott et al., "A Role for Tissue Factor in Cell Adhesion and Migration Mediated by Interaction with Actin–binding Protein 280", Mar. 9, 1998, J. Cell Biol., 140(5), pp. 1241–1253.*
Masuda et al., (1996) Eur. J. Immunol. 26:2529–2532.
Abstract Medline Accession No. 09277431.
Abstract Medline Accession No. 08687034.
Abstract Medline Accession No. 09499002.
Abstract Medline Accession No. 09462465.
Røttingen et al., (1995) J. of Biological Chem. 270(9):4650–4660.
Orthner et al., (1995) Blood 86(2) :436–443.

* cited by examiner

*Primary Examiner*—Jon P. Weber
(74) *Attorney, Agent, or Firm*—Reza Green, Esq.

(57) ABSTRACT

The present invention provides methods for modifying the motility of tissue factor (TF)-expressing cells, which are carried out by contacting such cells with an effective amount of Factor VIIai Factor VIIa agonist.

2 Claims, 20 Drawing Sheets

Lane 1.: MAPK protein
Lane 2.: 0 min - FVIIa + IL-1β
Lane 3.: 5 min + FVIIa + IL-1β
Lane 4.: 40 min + FVIIa + IL-1β
Lane 5.: 15 % FCS 15 min + IL-1β
Lane 6.: marker
Lane 7.: 0 min - FVIIa
Lane 8.: 5 min + FVIIa
Lane 9.: 40 min + FVIIa
Lane 10.: 15 % FCS 15 min Control MAPK antibody    phospho MAPK antibody 1. p44/42
2. FVIIa: 0 min
3. FVIIa: 3 min
4. FVIIa: 5 min
5. FVIIa: 7 min
6. FVIIa: 10 min
7. FVIIa: 40 min
8. Standards
9. 15% serum Activated form of MAPK Total amount of MAPK 1. Control
2. FVII
3. FVIIa
4. FVIIai
5. FVII S344A
6. FXa
7. Standards
8. 15% serum Activated form of MAPK Total amount of MAPK

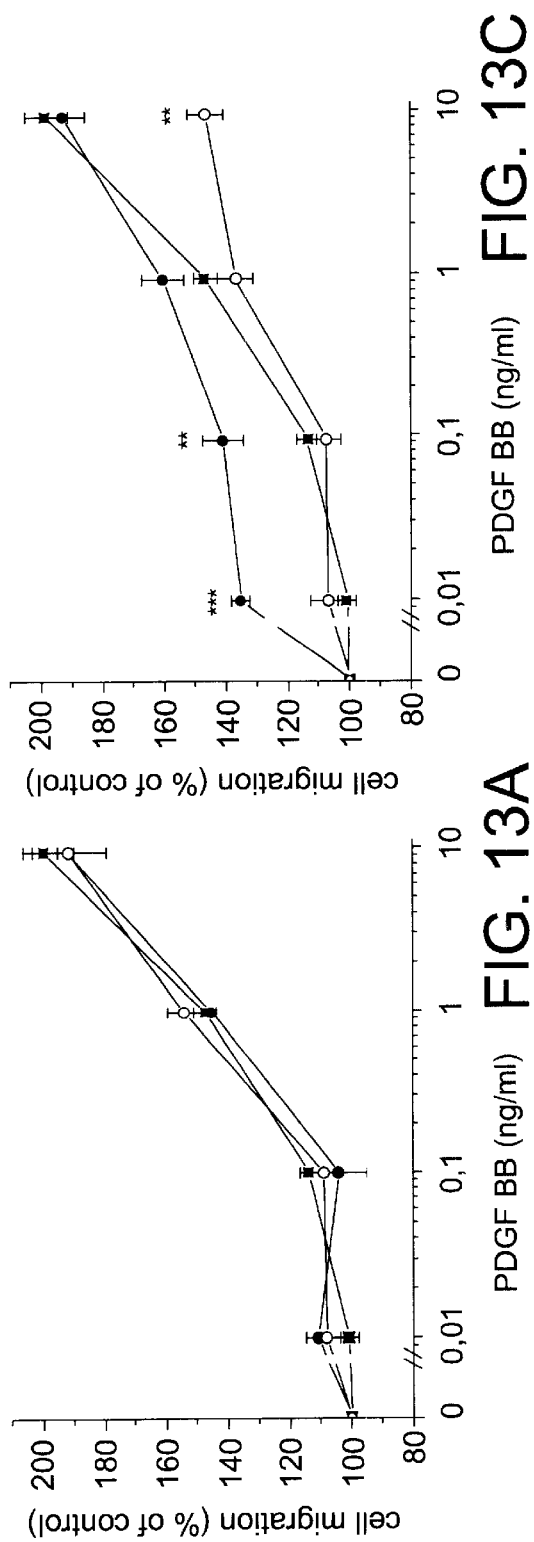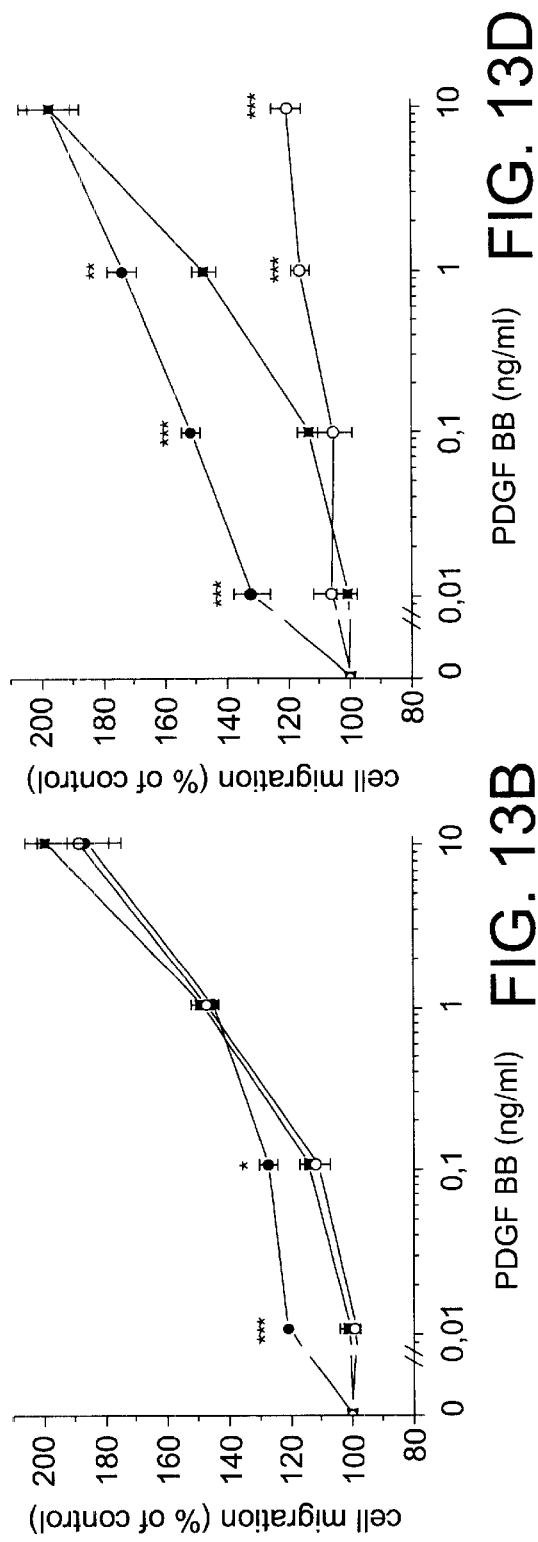

METHODS FOR MODIFYING CELL MOTILITY USING FACTOR VIIA OR INACTIVATED FACTOR VIIA

CROSS-REFERENCE TO RELATED APPLICATIONS

This application is a continuation-in-part of application Ser. No. 09/116,748 filed on Jul. 16, 1998 now U.S. Pat. No. 6,268,163 and claims priority under 35 U.S.C. 119 of Danish application Ser. No. 0879/97 filed Jul. 18, 1997, and of U.S. Provisional application Ser. No. 60/052,922 filed on Jul. 21, 1997, the contents of which are fully incorporated herein by reference.

FIELD OF THE INVENTION

A novel intracellular signalling activity of coagulation factor VII (FVII) in cells expressing tissue factor (TF) has been described. The present invention relates to use of FVIIa or another TF agonist, or FVIIai or another TF antagonist for the preparation of a medicament for modulation of FVIIa-induced activation of the MAPK signalling pathway in a patient. Moreover the present invention relates to a method of treatment, and a method of detecting the activity of compounds, in particular drug candidates, that interact with the FVIIa mediated intracellular signalling pathway.

BACKGROUND OF THE INVENTION

The extrinsic pathway of blood coagulation is initiated when FVIIa circulating in plasma binds to the integral-membrane protein, tissue factor (TF). The role of TF in blood coagulation has been extensively studied (Camerer, E., A. B. et al. *Thromb. Res.* 81:1–41, (1996)). The involvement of FVIIa as a proteolytic enzyme in the blood coagulation cascade is believed to be confined to the extracellular leaflet of TF expressing cells. An intracellular activity of FVIIa was first implied when the sequence of TF showed homology to the cytokine/interferon- or heamatopoietic receptor superfamily (Bassoon, J. F. *Proc. Natl. Acad. Sci. USA* 87: 6934–6938, (1990)). The subclass I of the heamotopoietic receptor family includes receptors for growth hormone, prolactin, interleukins 1 to 7, granulocyte-macrophage colony stimulating factors, erythropoitin and thrombopoitin. Subclass II includes TF and receptors for interferon a and b (Wells, J. A., and De Vos, A. M. *Annu. Rev. Biomol. Struct.* 22: 329–351, (1993)).

The resemblance of TF to this class of receptors was further substantiated with the appearance of the crystal structure (Harlos, K., D. M. A. et al. *Nature* 370: 662–666, (1994), Mueller, Y. A., M. H. et al. *Biochemistry* 33: 10864–10870 (1994) ). Characteristic of this class of cytokine receptors that includes receptors for interferon b and g and IL-10 (Mott, H. R. and Campbell, I. D. *Curr, Opin, Struct, Biol.* 5: 114–121, (1995)) is that their activation lead to rapid tyrosine phosphorylation of the receptors themselves, as well as a subset of intracellular proteins. Within minutes after the initial tyrosine phosphorylation an array of mitogen-activated (Ser/Thr) kinases (MAPK) is activated (Whitmarsh, A. J. and Davis, R. J. *J. Mol. Med.* 74:589–607, (1996)). These kinases are arranged in several parallel signalling pathways (David, M. et al. Science 269, 1721 (1996); Current opin. immunol. 8, 402–11 (1996)). Thorough studies of the putative intracellular signalling capacity of FVIIa have shown that it induces mobilization of intracellular free calcium ($Ca^{2+}$) in the human bladder carcinoma cell line, J82, which constitutively expresses TF and in umbelical vein endothelial cells which were pretreated with interleukin-1 to express TF (Rottingen, J.-A. et al. *J. Biol. Chem.* 270: 4650–4660, (1995)), but have failed to show any cytokine-like activation of intracellular tyrosine kinases (Camerer, E., et al. *J. Biol. Chem.* 271: 29034–29042, (1996)). In conclusion FVIIa is believed, in a TF dependent manner, to induce mobilization of intracellular $Ca^{2+}$ through activation of phospholipase C (Camerer, E., et al. *J. Biol. Chem.* 271: 29034–29042, (1996)). The mechanism by which FVIIa activates phospholipase C is not known, but Camerer et al. specifically ruled out tyrosine kinase activation.

SUMMARY OF THE INVENTION

The present invention relates to usage of FVII and/or FVIIa and/or another TF agonist and/or FVIIai and/or another TF antagonist in therapeutic treatment of pathological conditions that can be related to or treated by specific activation or inhibition of the FVIIa mediated intracellular signalling pathway.

In accordance with the present invention it has been shown that binding of FVIIa to its receptor TF induces activation of the mitogen-activated protein kinase (MAP kinase) pathway including phosphorylation of tyrosines in MAPK/Erk1. TF is known to play a pertinent role in the pathogenesis of a number of diseased states where regulatory interference at the intracellular level is believed to be beneficial.

Thus, diseased states which may be treated are pathological conditions such as mechanical injury of blood vessels, atherosclerosis, ischemia/reperfusion, bacterial infection, tumour deposition, or stimuli induced by "stress factors" such as cytokines, smoking, high blood pressure, high lipids- or glucose levels, advanced glycosylation endproducts, and bacterial lipopolysaccarides.

In another aspect, the invention encompasses methods for modifying cell motility or migration, which are carried out by contacting a tissue factor(TF)-expressing cell with a motility modifying-effective amount of a Factor VIIa; a Factor VIIa agonist; or a Factor VIIa antagonist, under conditions that result in modification of motility or migration. TF-expressing cells include, without limitation, fibroblasts, monocytes, macrophages, smooth muscle cells, endothelial cells, and tumor cells. To cause an increase in cell motility, Factor VIIa or an agonist thereof may be used. To cause a decrease, a Factor VIIa antagonist may be used, including, without limitation, Dansyl-Phe-Pro-Arg chloromethyl ketone-Factor VIIa; Danyl-Glu-Gly-Arg chloromethyl ketone-Factor VIIa; Dansyl-Phe-Phe-Arg chloromethyl ketone-Factor VIIa; or Phe-Phe-Arg chloromethyl ketone-Factor VIIa. These methods find utility in detection of effective treatments for pathological conditions involving inappropriate cell migration.

In yet another aspect, the invention provides methods for inhibiting cell migration in a patient suffering from a pathological condition associated with undesired cell migration, which are carried out by administering to the patient a migration-inhibitory-effective amount of a Factor VIIa antagonist. Administration may be via any appropriate route, including, without limitation, intravenous, intramuscular, and subcutaenous injection or by via direct injection into a tumor.

BRIEF DESCRIPTION OF THE DRAWINGS

FIGS. 13 A–D are graphic illustrations of the influence of different concentrations of FVIIa or FFR-FVIIa on PDGF-BB induced chemotaxis in fibroblasts.

DETAILED DESCRIPTION OF THE INVENTION

Figure 1:
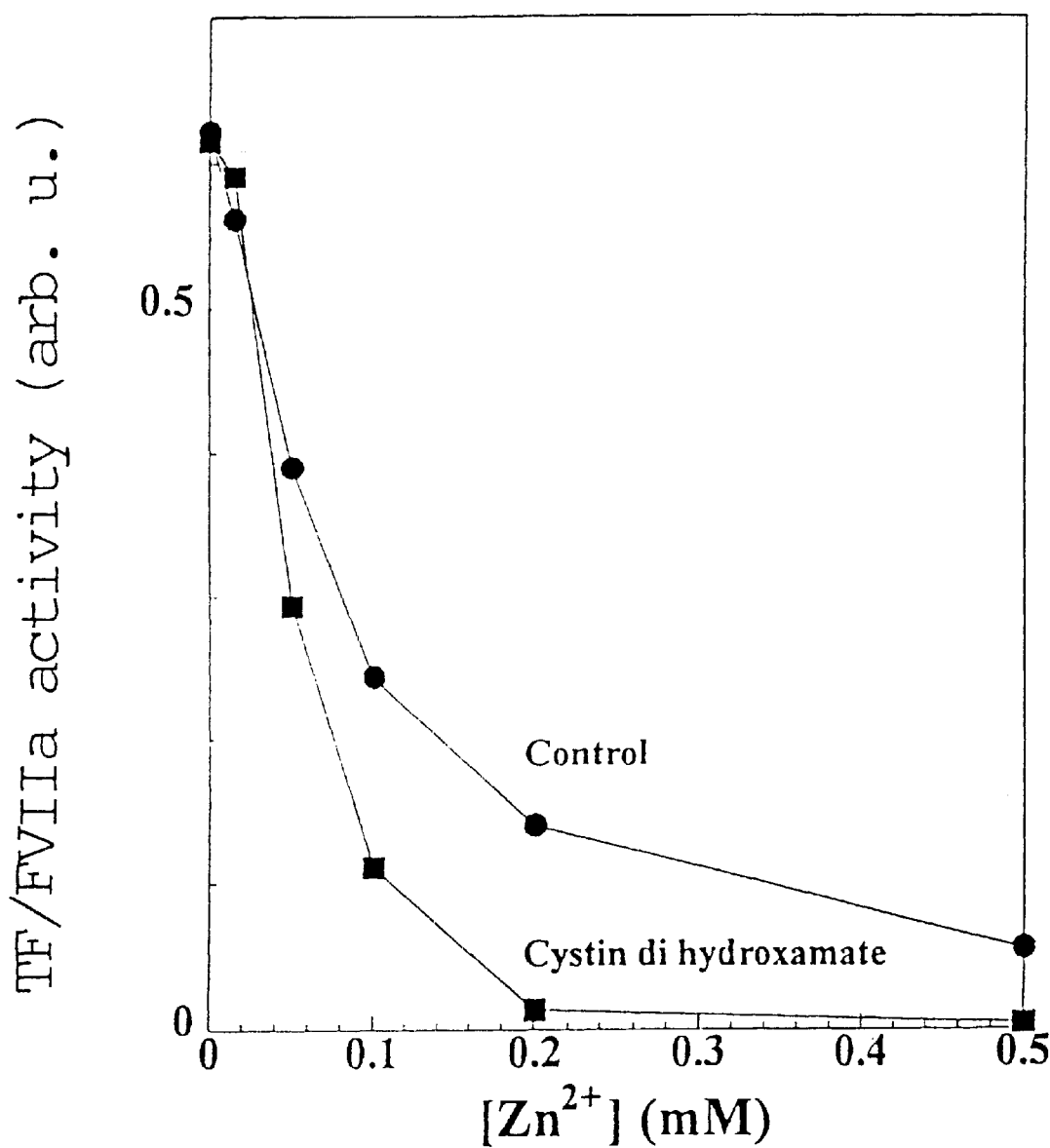
FIG. 1 shows the effect of zinc ions on TF-stimulated factor VIIa activity is shown in the absence (control) and presence of 0.2 mM cystin dihydroxamate. Factor VIIa activity was measured with the chromogenic substrate S2288 (H-D-Ile-Pro-Arg-p-nitroanilide). The activity of 10 nM FVIIa in the presence of 50 nM $TF_{1-218}$ (Dr W. Kisiel, University of New Mexico, Albuquerque, N. Mex.) was measured in buffer containing 50 mM TrisCl pH 7.4 0.1 M NaCl, 1 mM $CaCl_2$, 0.05% Tween 20 and 0.4 mM S2288. The activity was measured at room temperature as the change in absorbance at 405 nm.

The present invention relates to the use of FVII or FVIIa or another TF agonist for the manufacture of a pharmaceutical composition for inducing or enhancing activation of the MAPK signalling pathway in a patient, in particular wherein phosphorylation of MAPK/Erk/1/2 leads to activation of transcription factor Elk1.

The present invention also relates to the use of FVII, FVIIa or another TF agonist for the manufacture of a pharmaceutical composition for enhancing FVIIa-induced activation of the MAPK signalling pathway in a patient.

In a further aspect the present invention relates to the use of FVII, FVIIa or another TF agonist for the manufacture of a pharmaceutical composition for inducing or enhancing activation of transcription factor Elk1

In a still further aspect the present invention relates to the use of FVIIai or another TF antagonist for the manufacture of a pharmaceutical composition for inhibiting or preventing activation of the MAPK signalling pathway in a patient.

In a further aspect the present invention relates to the use of FVIIai or another TF antagonist for the manufacture of a pharmaceutical composition for inhibiting or preventing activation of transcription factor Elk1 in a patient.

In a still further aspect the present invention relates to the use of FVIIai or another TF antagonist for the manufacture of a pharmaceutical composition for inhibition or prevention of FVIIa-induced activation of the MAPK signalling pathway in a patient.

In an embodiment of the present invention it relates to the use of FVIIa or another TF agonist for the manufacture of a pharmaceutical composition for the treatment of re-endothelization, co-lateral revascularization in ischemia/reperfusion in myocardial infarction diabetic microangiopathy.

In another embodiment of the present invention it relates to the use of FVIIai or another TF antagonist for the manufacture of a pharmaceutical composition for the treatment of restenosis, cancer.

In a further aspect the present invention concerns a method for inducing or enhancing activation of the MAPK signalling pathway in a patient, which comprises administering an effective amount of FVII or FVIIa or another TF agonist to said patient. In one embodiment the activation leads to phosphorylation of MAPK/Erk1/2, which leads to activation of transcription factor Elk1.

In a still further aspect the present invention concerns a method for enhancing FVIIa-induced activation of the MAPK signalling pathway in a patient, which comprises administering an effective amount of FVII, FVIIa or another TF agonist to said patient. In a further aspect the present invention concerns a method for inducing or enhancing activation of transcription factor Elk1 in a patient, which comprises administering an effective amount of FVII or FVIIa or another TF agonist to said patient.

In a still further aspect the present invention concerns a method for inhibiting or preventing activation of the MAPK signalling pathway in a patient, which comprises administering an effective amount of FVIIai or another TF antagonist to said patient.

In a further aspect the present invention concerns a method for inhibiting or preventing activation of transcription factor Elk1 in a patient, which comprises administering an effective amount of FVIIai or another TF antagonist to said patient.

In a still further aspect the present invention concerns a method for inhibiting or preventing FVIIa-induced activation of the MAPK signalling pathway in a patient, which comprises administering an effective amount of FVIIai or another TF antagonist to said patient.

In a particular embodiment the effective amount is a daily dosage from about 5 $\mu$g/kg/day to about 500 $\mu$g/kg/day.

In a further embodiment the TF antagonist comprises a zinc-chelator which binds to FVIIa.

The present invention provides a mechanism for an intracellular activity of FVII and/or FVIIa that relates to stimulation of the MAPK signalling pathway. Such a mechanism provides the basis for establishing the involvement of FVII and/or FVIIa in pathological conditions in which TF expressing cells like endothelial cells, epithelial cells, fibroblasts, smooth muscle cells and monocytes/macrophages participate. The invention furthermore provides the basis for identifying specific pharmacological targets within the FVIIa mediated intracellular signalling pathway that are useful for therapeutic intervention.

Thus, the present invention relates to usage of FVII and/or FVIIa and/or FVIIai in therapeutic treatment of pathological conditions that can be related to or treated by specific activation or inhibition of the FVIIa mediated intracellular signalling pathway.

In accordance with the present invention it has been shown that binding of FVIIa to its receptor TF induces activation of the mitogen-activated protein kinase (MAP kinase) pathway including phosphorylation of tyrosines in MAPK/Erk1/2 leading to activation of transcription factor TFC/Elk1. TF is known to play a pertinent role in the pathogenesis of a number of diseased states where regulatory interference at the intracellular level is believed to be beneficial.

Modulation of FVIIa-induced signalling may be particularly useful at vascular sites where injury in its broadest sense leads to endothelial dysfunction. Such damage might include mechanical injury, atherosclerosis, ischemia/reperfusion, bacterial infection, tumour deposition, or stimuli induced by "stress factors" such as cytokines, smoking, high blood pressure, high lipids- or glucose levels, advanced glycosylation end-products, bacterial lipopolysaccarides e.t.c. All leading to vascular complications and endothelial dysfunction characterised at the cellular level by a complicated interplay between inflammatory cells, vascular cells and components of the coagulation system, the complement system and the fibrinolytic system. Leukocyte recruitment to such sites of dysfunctional endothelium is an important component of the host response to extravascular injury. At the location, release and surface expression of a number of leukocyte products serve to co-ordinate the inflammatory response. The local expression of TF on various cells, including monocytes, macrophages, fibroblasts, smooth muscle cells, endothelial cells and tumour cells is known to contribute significantly to the development of this response, and TF has been implicated as an important regulatory receptor in the development of various diseased states.

In another aspect, the present invention relates to a method of detecting drug candidates that modulate the FVIIa mediated intracellular signalling pathway, which method comprise
a) culturing a TF expressing cell that contain a DNA sequence coding for a reporter gene who's expression is regulated by a SRE promoter element
b) measuring the expression of the reporter gene
c) incubating the cell with a drug candidate, and
d) measuring the expression of the reporter gene produced by the incubated cell and determining any change in the level of expression compared to the expression measured in step b, such change being indicative of biologically active drug candidate in said cell, or the method comprise
e) culturing a TF expressing cell
f) measuring the level of protein phosphorylation of specific proteins in the FVIIa mediated intracellular signalling pathway
g) incubating the cell with a drug candidate, and
h) measuring the level of protein phosphorylation of the specific protein produced by the incubated cell and determining any change in the level of protein phosphorylation compared to the level measured in step f, such change being indicative of a biologically active drug candidate in said cell, or the method comprise
i) culturing a TF expressing cell
j) measuring the spatial localisation of a specific component of the FVIIa mediated intracellular signalling pathway that upon activation of the FVIIa mediated intracellular signalling pathway change intracellular localization
k) incubating the cell with a drug candidate, and
l) monitoring the localization of the same component and detect any change in localisation compared to the location measured in step j, such change being indicative of a biologically active drug candidate in said cell.

Generally, the blood components which participate in what has been referred to as the coagulation "cascade" are proenzymes or zymogens, enzymatically inactive proteins, which are converted to proteolytic enzymes by the action of an activator, itself an activated clotting factor. Coagulation factors that have undergone such a conversion and generally referred to as "active factors", and are designated by the addition of the letter "a" to the name of the coagulation factor (e.g. factor VIIa).

The term "zinc-chelator" is intended to comprise a compound that binds to factor VIIa and induces replacement of calcium ions with zinc ions within factor VIIa, thereby inhibiting the activity of factor VIIa or tissue factor-factor VIIa complex (TF-FVIIa).

A suitable TF antagonist according to the invention may be a zinc-chelating compound, e.g. a dihydroxamate or a dihydrazide with the hydroxamate or hydrazide groups located relative to each other in such a position that they are able to chelate a zinc ion. The zinc-chelating compound acts in combination with FVIIa. $Zn^{2+}$-ions exert their inhibitory action in competition with a stimulatory effect of $Ca^{2+}$-ions. It is predicted that $Zn^{2+}$-ions displace $Ca^{2+}$-ions from one or more calcium binding site(s) within FVIIa. Zinc-chelating compounds, e.g. hydroxamates and hydrazides, are capable of acting as powerfull supporters for binding of zinc ions in competition with calcium ions. Specific compounds thereby potentiate zinc inhibition of the activity of the factor VIIa/tissue factor complex. The activity of factor VIIa in complex with tissue factor can be inhibited by a mechanism in which a zinc chelator binds to factor VIIa and facilitates replacement of $Ca^{2+}$ with $Zn^{2+}$. By this action the chelator exerts a modulatory effect on TF at the normal concentration of free $Ca^{2+}$ and $Zn^{2+}$ ions in the blood.

Demonstration That a Suitable Chelator Potentiates Zinc Inhibition of Factor VIIa/tissue Factor Activity.

FIG. 1 shows that the effect of zinc ions to abolish FVIIa-TF complex formation is profoundly potentiated by the zinc chelator, cystindihydroxamate.

In one embodiment, the zinc-chelator is a compound of the general formula Ia

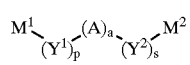
(Ia)

wherein $M^1$ is heteroaryl, a group of the formula

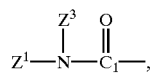

or a group of the formula

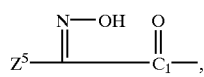

$M^2$ is heteroaryl, or a group of the formula

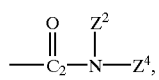

or a group of the formula

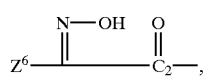

$Z^1$, $Z^2$, $Z^3$ and $Z^4$ independently of each other are hydrogen, $C_{1-4}$alkyl, hydroxy, amino or a valence bond attached to A, $Z^5$ and $Z^6$ represent a >C=O, which is attached to A, $Y^1$ and $y^2$ independently of each other are a group of the formula $—X^1\sim X^2\sim X^3—$, wherein $\sim$ independently of each other means a single or double bond, and $X^1$ represents >C=O, >CHR$^5$, >CH$_2$, >CH— or a valence bond, wherein R$^5$ is hydrogen, $C_{1-4}$alkyl, amino, $C_{1-4}$alkyl-amino, or di($C_{1-4}$alkyl)amino, $X^2$ represents —NH—, >N—, >CH$_2$ or >CH—, and $X^3$ represents —S—, >CH$_2$, >CH— or a valence bond, A is aryl or heteroaryl, p, a and s independently of each other are 0 or 1;

or a pharmaceutically acceptable salt thereof;

with the provisos that a+p+s is at least 1.

In one embodiment of the above compound of general formula Ia, $M^1$ and $M^2$ are independently of each other pyridinyl, such as pyridin-2-yl. In a preferred embodiment only one of $M^1$ and $M^2$ are pyridinyl, such as pyridin-2-yl.

In a second embodiment of the above compound of general formula Ia, $M^1$ is a group of the formula

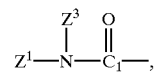

wherein $Z^1$ and $Z^3$ independently of each other are as defined above, or a group of the formula

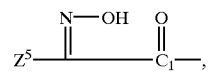

wherein $Z^5$ is a >C=O attached to A.

In a third embodiment of the above compound of general formula Ia, $M^2$ is a group of the formula

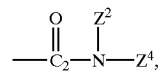

wherein $Z^1$ and $Z^4$ independently of each other are as defined above, or a group of the formula

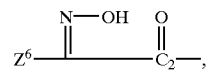

wherein $Z^6$ is a >C=O attached to A.

In a further embodiment of the above compound of general formula Ia, the distance between $C_1$ and $C_2$ is from about 0.37 nm to about 0.47 nm.

In a still further embodiment of the above compound of general formula Ia, the distance between $C_1$ and $C_2$ is from about 0.47 nm to about 0.57 nm.

In a further embodiment of the above compound of general formula Ia, the distance between $C_1$ and $C_2$ is from about 0.57 nm to about 0.67 nm.

In a still further embodiment of the above compound of general formula Ia, the distance between $C_1$ and $C_2$ is from about 0.67 nm to about 0.77 nm.

In a further embodiment of the above compound of general formula Ia, the distance between $C_1$ and $C_2$ is from about 0.37 nm to about 0.77 nm, preferably from about 0.40 nm to about 0.70nm, more preferred from about 0.40 mn to about 0.65 nm.

In a still further embodiment of the above compound of general formula Ia, $Z^1$, $Z^2$, $Z^3$ and $Z^4$ are independently of each other hydrogen, methyl, hydroxy, amino or a valence bond attached to A. Preferably $Z^1$, $Z^2$, $Z^3$ and $Z^4$ are independently of each other hydrogen, hydroxy, amino or a valence bond attached to A.

In a further embodiment of the above compound of general formula Ia, $Y^1$ and $Y^2$ are independently of each other a group of the formula —$X^1$~$X^2$~$X^3$—, wherein~independently of each other means a single or double bond, and $X^1$ represents >C=O, >CHR$^5$, >CH$_2$, >CH— or a valence bond, wherein R$^5$ is hydrogen, methyl, amino, methylamino, or di-methylamino, $X^2$ represents —NH—, >N—, >CH$_2$ or >CH—, and $X^3$ represents —S—, >CH$_2$, >CH— or a valence bond. Preferably $X^1$ is >C=O, >CHR$^5$ or a valence bond, wherein R$^5$ is amino, $x^2$ is —NH—or >CH$_2$ and $X^3$ is —S— or a valence bond.

In a still further embodiment of the above compound of general formula Ia, A is phenyl, 1,2,3-triazolyl, 1,2,4-triazolyl, or pyrazolyl.

In a particular embodiment of the above compound of general formula Ia, the compound is selected from:

1-hydroxy-7-hydroxycarbamoylquinoxaline-2,3(1H,4H)-dione, having the formula III

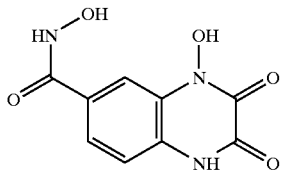

(III)

5-(2-pyridyl)-1,2,4-triazole-3-carbohydrazide, having the formula IV

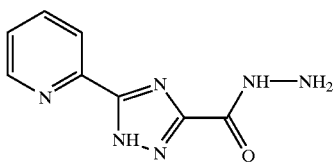

(IV)

1,2,3-triazole-4,5-dicarbohydrazide, having the formula V

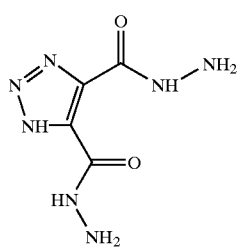

(V)

Pyrazole-3,5-dicarbohydroxamic acid, having the formula VI

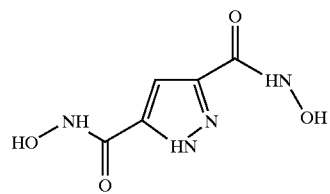

(VI)

4,7-Dihydro-[4,7]phenanthroline-1,2,3,8,9,10-hexaone-2,9-dioxime, having the formula VII

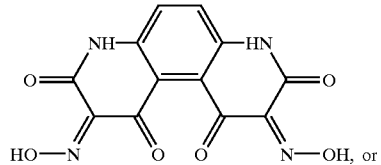

(VII)

L-Cystine dihydroxamate, having the formula VIII

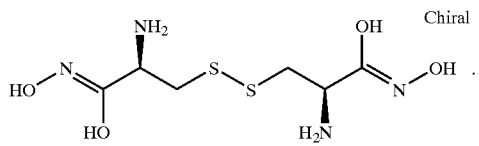

(VIII)

Definitions

The term "FVII" means "single chain" coagulation factor VII

The term "Factor VIIa", or "FVIIa" means "two chain" activated coagulation factor VII cleaved by specific cleavage at the Arg152-Ile153 peptide bond. FVIIa, may be purified from blood or produced by recombinant means. It is evident that the practice of the methods described herein is independent of how the purified factor VIIa is derived and, therefore, the present invention is contemplated to cover use of any factor VIIa preparation suitable for use herein. Preferred are human FVIIa.

The term "FVIIai" is intended to mean FVIIa having at least one modification in its catalytic center, which modification substantially inhibits the ability of modified FVIIa to activate FX and FIX. Such modification includes amino acid substitution of one or more of the catalytic triad residues Ser344, Asp142 and His193, and also includes modification of catalytic triad residues with serine protease inhibitors such as organophosphor compounds, sulfanylfluoride, peptide halomethyl ketone or azapeptide. FFR ck FVIIa is one example of a FVIIai derivative obtained by blocking of the active center of FVIIa with the irreversible inhibitor, D-phenylalanine-L-phenylalanine-L-argininine chloromethyl ketone.

The term "protein kinase" is intended to indicate an enzyme that is capable of phosphorylating serine and/or threonine and/or tyrosine in peptides and/or proteins.

The term "MAPK signalling pathway" is intended to mean a cascade of intracellular events that mediate activation of Mitogen-Activated-Protein-Kinase (MAPK) and homologues thereof in response to various extracellular stimuli. Three distinct groups of MAP kinases have been identified in mammalian cells: 1) extracellular-regulated kinase (Erk), 2) c-Jun N-terminal kinase (JNK) and 3) p 38 kinase. The Erk MAP kinase pathway involves phosphorylation of Erk 1 (p 44) and/or Erk 2 (p 42). Activated Erk MAP kinases translocate to the nucleus where they phosphorylate and activate transcription factors including (Elk 1) and signal transducers and activators of transcription (Stat).

The term "FVIIa-induced activation of the MAPK signalling pathway" is intended to indicate that FVIIa binds to TF in a mammalian cell and thereby induce activation of transcription factors Elk1 and Stat elements in a mammalian cell via phosphorylation of MAPK/Erk1/2.

The term "FVIIa mediated intracellular signalling pathway" is intended to indicate a cascade of intracellular events that involve activation of Erk1/2 MAPK.

The term "drug candidate" is intended to indicate any sample which has a biological function or exerts a biological effect in a cellular system. The sample may be a sample of a biological material such as a microbial or plant extract, or it may be a sample containing a compound or mixture of compounds prepared by organic synthesis or genetic techniques.

The term "TF agonist" comprises compounds inducing
a) signal transduction by direct binding to TF (e.g. FVIIa),
b) stimulation of MAPK cascade,
c) abrogation of MAPK inhibition (e.g. PTPase inhibitors),
which agonists are drug candidates as defined above.

The term "TF antagonist" comprises
a) reagents which compete with FVIIa for binding to TF without transmission, e.g. FVIIai,
b) reagents which bind to FVIIa and prevent binding to TF, e.g. Zn hydroxamate,
c) reagents which inhibit signal transduction by interfering with members of the MAPK cascade,
which antagonists are drug candidates as defined above.

The term "pharmacological targets" is intended to indicate a protein that can alter the activity of the FVIIa mediated intracellular signalling pathway.

The term "reporter gene" is intended to indicate a DNA construct that, when transcribed, produces a protein that can be detected.

The term "transcription factor TFC/Elk1" or "transcription factor Elk1" is intended to comprise Elk1 (also known as p62 ternary complex factor, TFC) is an Ets-related transcription factor that mediates growth factor stimulation of the c-fos promoter. Elk1 binds to DNA in part via interaction with Serum Response Factor. Elk1 is a bona fide Erk substrate. SAPKs phosphorylation of Elk1 may mediate transcriptional activation of the fos promotor in response to a variety of stresses.

The term "SRE promoter element" means a DNA sequence that binds transcription factors induced by components present in serum.

The term "TF expressing cell" mean any mammalian cell, that expresses TF.

The term "protein phosphorylation" is intended to indicate phosphorylation of serine and/or threonine and/or tyrosine in peptides and/or proteins.

Modulation of FVIIa-induced activation of the MAPK signalling pathway in a patient is defined as the capacity of FVIIa or another TF agonist, or FVIIai or another TF antagonist to 1) either increase or decrease ongoing, normal or abnormal, signal transduction, 2) initiate normal signal transduction, and 3) initiate abnormal signal transduction.

In this context, the term "treatment" is meant to include both prevention of an adverse condition, such as restenosis, and regulation of an already occurring condition, such as bacterial infection, with the purpose of inhibiting or minimizing the condition. Prophylactic administration of FVIIa or another TF agonist, or FVIIai or another TF antagonist is thus included in the term "treatment".

In this context, the term "one unit" is defined as the amount of factor VII present in 1 ml of normal plasma, corresponding to about 0.5 $\mu$g protein. After activation 50 units correspond to about 1 $\mu$g protein.

In this context, the term "patient" is defined as any animal, in particular mammals, such as humans, suffering from a condition which may be treated by inhibition or activation of the MAPK signalling pathway.

Abbreviations

TF tissue factor

FVII factor VII in its single-chain, unactivated form

FVIIa factor VII in its activated form rFVIIa recombinant factor VII in its activated form FVIIai modified factor VII Pharmaceutical Administration The regimen for any patient to be treated with FVIIa or another TF agonist or FVIIai or another TF antagonist as mentioned herein should be determined by those skilled in the art. The daily dose to be administered in therapy can be determined by a physician and will depend on the particular compound employed, on the route of administration and on the weight and the condition of the patient. An effective amount is suitably a daily dosage from about 5 $\mu$g/kg/day to about 500 $\mu$g/kg/day, preferably from about 10 $\mu$g/kg/day to 300 $\mu$g/kg/day, more preferred from about 15 $\mu$g/kg/day to 200 $\mu$g/kg/day, most preferred from about 20 $\mu$g/kg/day to 100 $\mu$g/kg/day.

The FVIIa or another TF agonist or FVIIai or another TF antagonist should be administered in one single dose, but it can also be given in multiple doses preferably with intervals of 4–6–12 hours depending on the dose given and the condition of the patient.

The FVIIa or another TF agonist or FVIIai or another TF antagonist may be administered intravenously or it may be administered by continuous or pulsatile infusion. FVIIa or another TF agonist or FVIIai or another TF antagonist is preferably administered by intravenous injections and in an amount of about 100–100,000 units per kg body weight, and preferably in an amount of about 250–25,000 units per kg body weight corresponding to about 5–500 $\mu$g/kg, a dose that may have to be repeated 2–4 times per 24 hours.

Pharmaceutical Compositions

Conventional techniques for preparing pharmaceutical compositions which can be used according to the present invention are, for example, described in *Remington's Pharmaceutical Sciences*, 1985.

The compositions used according to this invention are prepared by methods known per se by the skilled art worker.

In short, pharmaceutical preparations suitable for use according to the present invention is made by mixing FVII, FVIIa or another TF agonist or FVIIai or another TF antagonist, preferably in purified form, with suitable adjuvants and a suitable carrier or diluent. Suitable physiological acceptable carriers or diluents include sterile water and saline. Suitable adjuvants, in this regard, include calcium, proteins (e.g. albumins), or other inert peptides (e.g. glycylglycine) or amino acids (e.g. glycine, or histidine) to stabilise the purified factor VIIa. Other physiological acceptable adjuvants are non-reducing sugars, polyalcohols (e.g. sorbitol, mannitol or glycerol), polysaccharides such as low molecular weight dextrins, detergents (e.g. polysorbate) and antioxidants (e.g. bisulfite and ascorbate). The adjuvants are generally present in a concentration of from 0.001 to 4% w/v. The pharmaceutical preparation may also contain protease inhibitors, e.g. apronitin, and preserving agents.

The preparations may be sterilized by, for example, filtration through a bacteria-retaining filter, by incorporating sterilising agents into the compositions, by irradiating the compositions, or by heating the compositions. They can also be manufactured in the form of sterile solid compositions which can be dissolved in sterile water, or some other sterile medium suitable for injection prior to or immediately before use.

The present invention is further illustrated by the following examples which, however, are not to be construed as limiting the scope of protection. The features disclosed in the foregoing description and in the following examples may, both separately and in any combination thereof, be material for realizing the invention in diverse forms thereof.

EXAMPLE

Preparation of Compound

Human purified factor VIIa suitable for use in the present invention is preferably made by DNA recombinant technology, e.g. as described by Hagen et al., *Proc.Natl.Acad.Sci. USA* 83: 2412–2416, 1986 or as described in European Patent No. 200.421 (ZymoGenetics). Factor VIIa produced by recombinant technology may be authentic factor VIIa or a more or less modified factor VIIa provided that such factor VIIa has substantially the same biological activity for blood coagulation as authentic factor VIIa. Such modified factor VIIa may be produced by modifying the nucleic acid sequence encoding factor VII either by altering the amino acid codons or by removal of some of the amino acid codons in the nucleic acid encoding the natural FVII by known means, e.g. by site-specific mutagenesis.

Factor VII may also be produced by the methods described by Broze and Majerus, *J.Biol.Chem.* 255 (4): 1242–1247, 1980 and Hedner and Kisiel, *J.Clin.Invest.* 71: 1836–1841, 1983. These methods yield factor VII without detectable amounts of other blood coagulation factors. An even further purified factor VII preparation may be obtained by including an additional gel filtration as the final purification step. Factor VII is then converted into activated FVIIa by known means, e.g. by several different plasma proteins, such as factor XIIa, IX a or Xa. Alternatively, as described by Bjoern et al. (Research Disclosure, 269 September 1986, pp. 564–565), factor VII may be activated by passing it through an ion-exchange chromatography column, such as Mono Q® (Pharmacia fine Chemicals) or the like.

The following compounds are obtained from the indicated companies or universities:

5-(2-Pyridyl)-1,2,4-triazole-3-carbohydrazide (Obtained from Maybridge Chemicals LTD (SEW 00446))

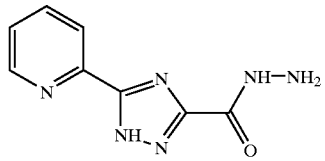

1,2,3-Triazole-4,5-dicarbohydrazide (obtained from Odense University; is also Disclosed in Farmaco, 50,(2) 1995, 99–106)

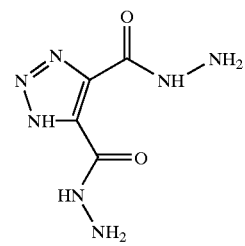

4,7-Dihydro-[4,7]phenanthroline-1,2,3,8,9, 10-hexaone-2, 9-dioxime (obtained from Labotest under the number (LT-2 AM36))

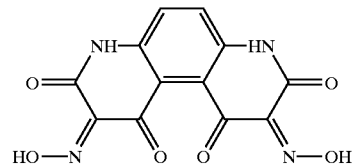

Example 1

Preparation of 1-Hydroxy-7-hydroxycarbamoylquinoxaline-2,3(1H,4H)-dione a) 4-Ethoxalylamino-3-nitrobenzoic Acid Anhydrous triethylamine (22.6 ml, 0.162 mol) was added to a solution of 4-amino-3-nitrobenzoic acid (14.4 g, 0.081 mol) in a mixture of dry tetrahydrofuran (300 ml) and dry N,N-dimethylformamide (100 ml). Then a solution of ethyl oxalylchloride (18 ml, 0.162 mol) in 100 ml of dry tetrahydrofuran was added dropwise at 0° C. The mixture was stirred overnight at room temperature and triethylamine hydrochloride was removed by filtration. The filtrate was evaporated to dryness and the residue was triturated with water. The crude product was isolated by filtration and recrystallised from ethanol to give 14.4 g of the title compound which was used without further purification in the subsequent reductive cyclisation reaction. $^1$H-NMR (DMSO-d$_6$): 1.35 (t, J=7 Hz, 3H, CH$_3$), 4.36 (q, J=7 Hz, 2H, CH$_2$), 8.2–8.6 (m, 3H, ArH), 11.6 (s, 1H, NH).

b) 7-Carboxy-1-hydroxyquinoxaline-2,3(1H,4H)-dione

A solution of 4-ethoxalylamino-3-nitrobenzoic acid (14.0 g, 49.6 mmol) in 800 ml of N,N-dimethylformamide was hydrogenated at room temperature and atmospheric pressure in the presence of 1.3 g of 5% platinum on carbon for 2.5 h. The catalyst was filtered off and washed with N,N-dimethylformamide. The filtrate was evaporated to dryness and the residue was triturated with 500 ml of water and filtered. The crude product was dissolved in 900 ml of 1M potassium dihydrogen phosphate buffer (pH 7.4), filtered and reprecipitated with 6 M hydrochloric acid to yield 7.7 g (70%) of the title compound. $^1$H-NMR (DMSO-d$_6$): 7.25 (d, J=9 Hz, 1H, ArH), 7.75 (dd, J=9 Hz, 2 Hz, 1H, ArH), 7.98 (d, J=2 Hz, 1H, ArH), 12.3 (br.s, 1H, exchangeable).

c) 1-Benzyloxy-7-carboxyquinoxaline-2,3(1H,4H)-dione

7-Carboxy-1-hydroxyquinoxaline-2,3(1H,4H)-dione (2.22 g, 10 mmol) was dissolved in a mixture of 50 ml of 1M potassium dihydrogen phosphate buffer (pH 7.4) and 25 ml of ethanol by gently heating. To the cooled mixture was added 1.19 ml (10 mmol) of benzylbromide and the mixture was stirred overnight at room temperature. The precipitate was isolated by filtration and washed with ethanol. The crude product was triturated with 4M hydrochloric acid and washed with water and dried in vacuo to give 1.56 g (50%)

of the title compound. $^1$H-NMR (DMSO-d$_6$): 5.22 (s, 2H, CH$_2$), 7.2–7.9 (m, 8H, ArH), 12.35 (s, 1H, exchangeable), 13.05 (br.s, 1H, exchangeable).

d) 1-Benzyloxy-7-(benzyloxycarbamoyl)quinoxaline-2,3 (1H,4H)-dione

To an ice-cooled solution of 1-Benzyloxy-7-carboxyquinoxaline-2,3(1H,4H)-dione (422 mg, 1.35 mmol) in 10 ml of N,N-dimethylformamide was added 1-hydroxybenzotriazole (218 mg, 1.48 mmol) followed by 1-(3-dimethylaminopropyl)-3-ethylcarbodiimide hydrochloride (272 mg, 1.42 mmol). Stirring was continued for 30 min at 0° C. and O-benzylhydroxylamine hydrochloride (237 mg, 1.49 mmol) and dry triethylamine (0.21 ml, 1.5 mmol) was added. The mixture was stirred overnight at room temperature, then cooled and filtered. The isolated solid was successively washed with water, saturated aqueous sodium hydrogen carbonate and water. Recrystallisation from ethanol gave 290 mg (51%) of the title compound. $^1$H-NMR (DMSO-d$_6$): 4.95 (s, 2H, CH$_2$), 5.19 (s, 2H, CH$_2$), 7.2–7.8 (m, 13H, ArH), 11.8 (br.s, 1H, exchangeable), 12.3 (br.s, 1H, exchangeable).

e) 1-Hydroxy-7-hydroxycarbamoylquinoxaline-2,3(1H, 4H)-dione

A suspension of 1-Benzyloxy-7-(benzyloxycarbamoyl)quinoxaline-2,3(1H,4H)-dione (250 mg, 0.6 mmol) in 50 ml of ethanol was hydrogenated at atmospheric pressure and room temperature for 1 h in the presence of 50 mg of 5% palladium on carbon. Water (20 ml) and 4 ml of 2 N sodium hydroxide was added to dissolve the product and the catalyst was removed by filtration. The filtrate was acidified with 4 ml of 4M hydrochloric acid, evaporated to about 10 ml and filtered to give a white solid. Washing with a small amount of cold water and ethanol yielded 109 mg (70%) of the title compound. $^1$H-NMR (DMSO-d$_6$): 7.21 (d, J=8 Hz, 1H, ArH), 7.60 (dd, J=8 Hz, 2 Hz, 1H, ArH), 7.90 (d, J=2 Hz, 1H, ArH), 9.05 (br.s, 1H, exchangeable), 11.35 (br.s, 1H, exchangeable), 11.82 (br.s, 1H, exchangeable), 12.35 (br.s, 1H, exchangeable).

Example 2

Synthesis of Pyrazole-3.5-dicarbohydroxamic Acid (28–3028) on Solid Phase:

a) Synthesis of the linkage[1]: a) Sasrin® resin (10.0 g, 0.73 mmol/g) was swelled in dichloromethane (40 mL) and diisopropylethylamine (40 mL), and cooled to 0° C. A solution of methanesulfonyl chloride (5.0 mL, 7.40 g, 64.6 mmol) in dichloromethane (20 mL) was added dropwise while stirring under argon, and stirring was continued for 30 min at 0° C. and for 45 min at 25° C. Subsequently, the resin was drained and washed with dichloromethane (3 portions of 80 mL) and N-methylpyrrolidinone (NMP; 3 portions of 80 mL). b) In a 500 mL flask equipped with a mechanical stirrer, N-hydroxyphthalimide (23.8 g, 146 mmol) was dissolved in NMP (280 mL), and cesium carbonate (27.7 g, 73 mmol) was added. The mesylated resin was added in small portions at 25° C., and stirring was continued for 30 min at 25° C. and for 16 h at 80° C. The chocolate-brown reaction mixture was poured into a Buchner funnel and washed extensively with methanol, water, methanol, dichloromethane, until the resin was colorless. c) The resin was suspended in ethanol (70 mL), anhydrous hydrazine (8 mL) was added, and the mixture was shaken at 25° C. for 16 h. The resin was washed extensively with methanol, dichloromethane, methanol and dried; yield 9.50 g (95%).

b) Attachment of pyrrole-3,5-dicarboxylic acid to the resin prepared above: 0.10 g of the resin synthesized above was washed with N-methylpyrrolidone (1.5 mL). Subsequently, pyrrole-3,5-dicarboxylic acid (155 mg, 1.0 mmol), NMP (0.90 mL), 4-N,N-dimethylaminopyridine (20 mg) in NMP (0.10 mL) and diisopropylcarbodiimide (78 µL, 0.5 mmol) were added, and the mixture was shaken at r.t. for 120 min. Subsequently, the mixture was washed with NMP (4 portions of 2 mL).

c) A solution of PyBOP® (0.5 mmol, 260 mg) in NMP (250 µL) was added to the resin. To this, a solution of hydroxylamine hydrochloride (70 mg, 1 mol) in NMP (0.80 mL)/N-methylmorpholine (0.20 mL) was added, and the mixture was shaken at room temperature for 30 min. Subsequently, the resin was washed with dimethylformamide (3 portions of 2 mL) and dichloroethane (5 portions of 2 mL).

d) Cleavage: The resin was washed with dichloroethane (2 ML), and a mixture of 25% trifluoroacetic acid in dichloroethane (1.0 mL) was added. The mixture was shaken at r.t. for 15 min. The resin was filtered, the filtrate was collected, and the resin was washed with acetonitrile (2 portions of 0.80 mL). The solvents were evaporated in vacuo, and the crude samples were submitted to assay.

Lit.: L. S. Richter, M. C. Desai, *Tetrahedron Lett.* 1997, 38, 321.

Example 3

Treatment of Atherosclerosis:

Histochemical studies suggest that TF is a major determinant of the pro-thrombotic activity of human atherosclerotic lesions (Fernandez-Ortiz, A. et al. *J. Am. Coll. Cardiol.* 1562–1569, (1994)). Initiation of the coagulation cascade resulting in thrombin generation is important for fibrin deposition and the atherogenesis of the plaque. It is likely that also the cellular response caused by TF-dependent signalling described in the present invention has important implications for atherogenesis and plaque development.

Example 4

Treatment of Angina and Myocardial Infarction:

TF is expressed on macrophages/foam cells associated with atherosclerotic plaques, and rupture of these structures are key events in the pathogenesis of unstable angina and myocardial infarction. It has been found that TF antigen concentration and activity in plaques from patients with unstable angina or myocardial infarction was significantly higher than in those from patients with stable angina (Ardissino, D. et al. *The Lancet* 349: 769–771, (1997)). It is desirable to be able to interfere with and modulate the biological effects of TF expression to prevent a vicious spiral involving TF, whether this is caused by triggering of the coagulation system or it is a result of cellular signalling and consecutive reactions.

Example 5

Treatment of Cancer/Angiogenesis:

TF is expressed on endothelial cells and tumour cells in breast cancer, but not on the same cells in benign fibrocystic breast disease (Contrino, J., *Nature Med.* 2: 209–215, (1996)). Local exposure of TF on the surface of specific cells in tumours appears to be crucial for vascularisation and growth of tumours (Folkman, J. *Nature Med.* 2: 167–168, 1996)). Recent studies have shown that blocking of a tumours blood supply with the angiogenesis inhibitors, angiostatin (O'Reilly, M. S. et al. *Cell* 79, 315–328(1994); Folkman, J. *Nature Med.* 1, 27–31(1995), WO9641194-A1) and endostatin (O'Reilly, M. S. et al. *Cell* 88; 277–285 (1997)), or with antibody-directed targeting of TF (Huang, X. et al., *Science* 275: 547–550, (1997)) can arrest tumour or even cause tumour regression. Cellular signalling and orchestration of cellular transmitter substances is an important aspect of vascularization and tumour biology, and TF is likely to be of central importance in these processes. Reagents which modulate FVIIa-induced signalling is likely to work by a distinctly different mechanism and can provide an alternative to presently known angiogenic inhibitors.

Example 6
Treatment of Restenosis After Clearing of Blocked Atherosclerotic Vessels by Surgical Procedures.

Mechanical injury of the vessel wall results in local exposure of TF important to haemostasis and subsequent tissue repair. This is of immediate interest in relation to clearing of blocked atherosclerotic vessels by surgical procedures such as angioplasty, endarterectomy, reduction arterectomy or bypass grafting. These procedures result in serious vessel injury, TF exposure, thrombus formation and subsequent healing reactions. Proliferation of smooth muscle cells (SMCs) in the vessel wall is an important aspect of these events. The injury of the vessel is followed by medial SMC proliferation and migration into the intima, which characteristically occurs within the first few weeks and up to six month after injury and stops when the overlaying endothelial layer is established. In about 30% or more of patients treated by angioplasty, endarterectomy or bypass grafts, thrombosis and/or SMC proliferation in the intima causes re-occlusion of the vessel and consequent failure of the reconstructive surgery. This closure of the vessel subsequent to surgery is known as restenosis. Modified factor VIIa (FVIIai) has been shown to effectively suppress the restenosis process (cf. WO 92/15686, title: modified FVII). This effect might be due to an inhibition of clot formation and thrombin generation initially after treatment of the constricted vessel. However, the present invention shows that in addition to being an antithrombotic drug, FVIIai is also an inhibitor of TF-dependent cellular signalling. Suppression of restenosis by FVIIai might therefore occur as a result of an effect on SMC proliferation or other cellular activities, and drugs which works as effectors of FVIIa-induced signalling could therefore represent a new and better strategy for the treatment of restenosis.

Example 7
Reporter Gene Response: Activation of SRE Reporter Gene Expression Induced by FVIIa Upon Binding to the Human TF.

Figure 2A:
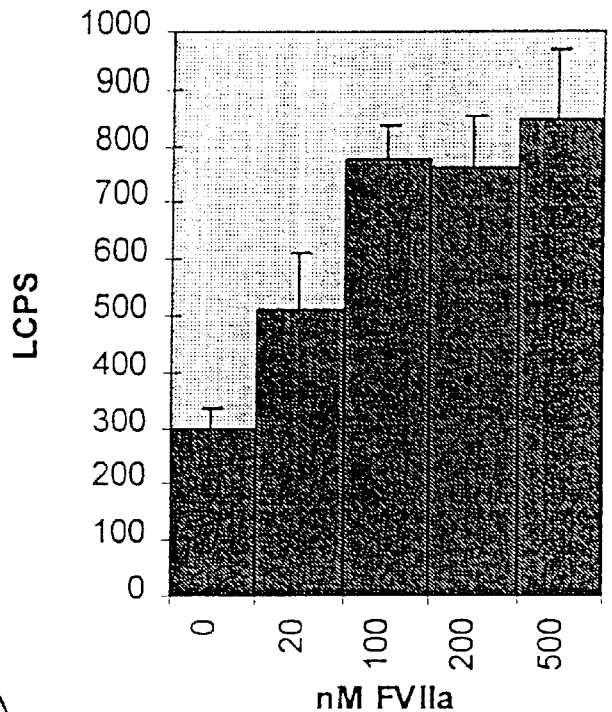
FIGS. 2A and 2B show the activation of SRE reporter gene expression induced by FVIIa upon binding to human TF.
Figure 2B:
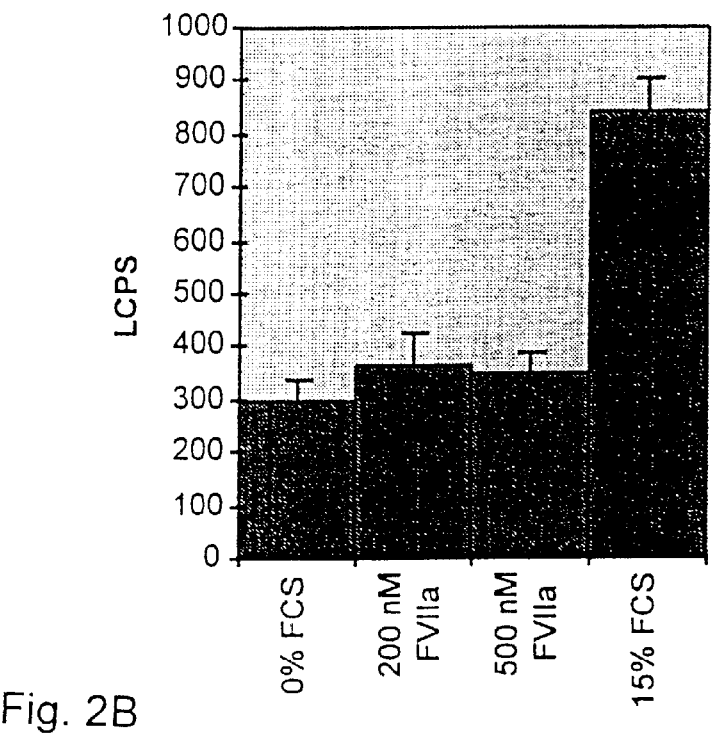

BHK cells with and without stably transfected TF were stably transfected with KZ136 (reporter construct encoding 2×STAT1,3), 2×(STAT4,5,6) and a serum response element (SRE) upstream to a luciferase reporter gene) were stimulated with FVIIa. Only cells expressing TF responded to FVIIa in a dose dependent manner. FIG. 2A shows that 20 nM FVIIa induced a response which was approximately two times higher than the background level. A maximal inducible FVIIa-response, three times higher than the background level, was reached at 100 nM FVIIa. FIG. 2B shows that BHK cells not expressing TF did not respond to FVIIa addition. The responsiveness of the reporter system was controlled by addition of 15% FCS which showed a 3 times increase in luciferase activity over non-stimulated cells.

Example 8
Monitoring the Signalling Pathway Induced Upon FVIIa—TF Binding: The Reporter Gene Approach.

A set of reporter vectors were stably transfected by selection into BHK cells already stably transfected with a construct driving expression of the TF. The constructs were KZ131, encoding one serum response element upstream to a luciferase reporter gene, KZ134, encoding a cassette of two STAT1,3 elements and two STAT4,5,6 elements upstream to a luciferase reporter gene, KZ136, encoding a cassette of two STAT1,3 elements, two STAT4,5,6 elements and one serum response element upstream to a luciferase reporter gene, and KZ142, encoding the c-jun promoter upstream to a luciferase reporter gene. Cells transfected with KZ131, KZ134 and KZ136 responded upon addition of FVIIa to the cells but cells transfected with KZ142 did not. Since the P44/42 MAPK pathway stimulates serum response elements and STAT elements these results indicate that TF upon binding of FVIIa activates the p44/42 MAPK pathway. The classical p44/42 MAPK do not activate the c-jun promoter.

Example 9
Monitoring the Signalling Pathway Induced Upon FVIIa—TF Binding: The MEK1/2 Inhibitor Approach.

Figure 3:
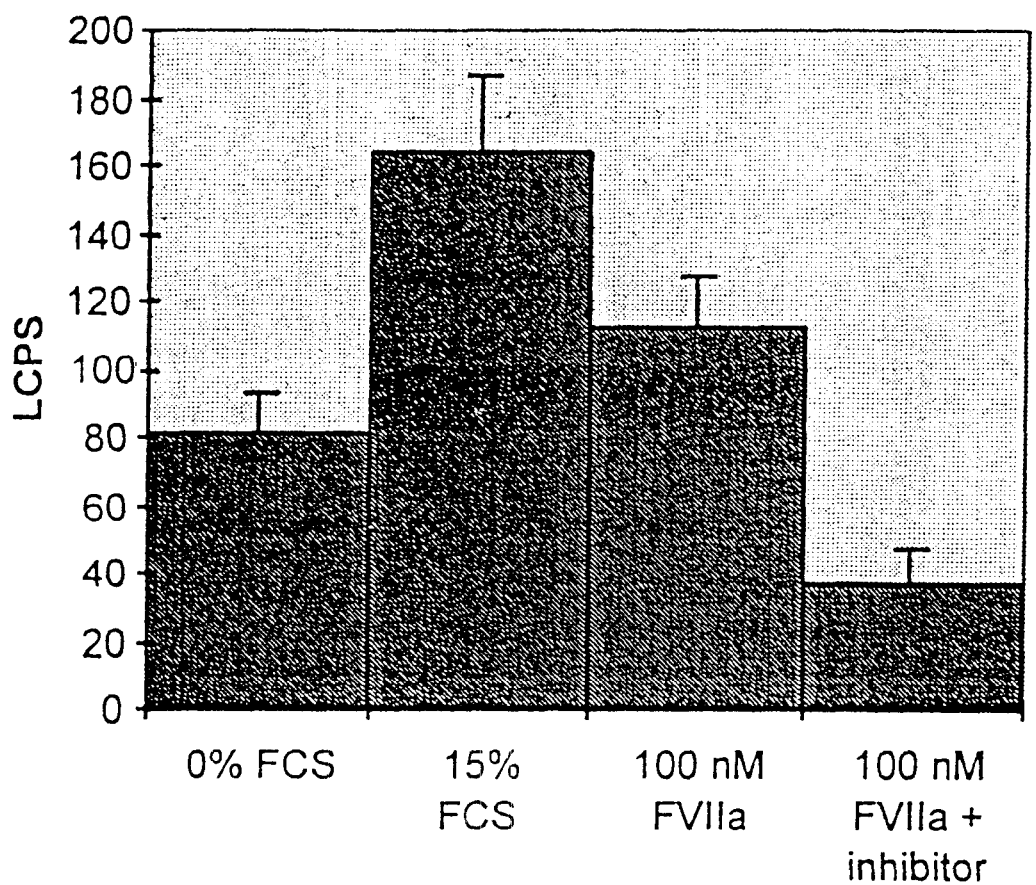
FIG. 3 shows the stimulation of BHK-TF/KZ136 cells stimulated with FVIIa with and without prior treatment with the MEK1/2 inhibitor PD98059. PB98059 was maintained at 50 μM throughout the experiment.

PD98059 is a specific inhibitor of MEK1, a kinase specifically involved in the p44/p42 MAPK cascade. BHK cells stably transfected with TF and the KZ136 reporter construct pre-treated with 50 µM PD98059 for one hour prior to stimulation with 100 nM FVIIa did not respond. Cells not pre-treated with PD98059 did respond well (FIG. 3) showing that TF is signalling through the p44/42 MAPK pathway.

Example 10
Monitoring the Signalling Pathway Induced Upon FVIIa—TF Binding: The Two Hybrid Approach.

Figure 4A:
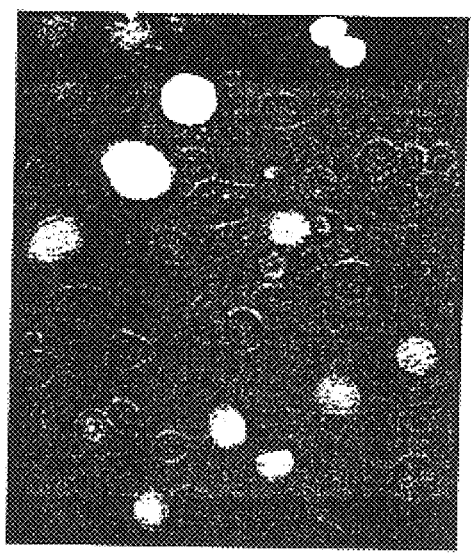
FIGS. 4A and 4B show the specific activation of the Elk1 transcriptional factor: 4A) Superimposition of the transmitted light image and the fluorescence image showing the transfection efficiency,4B) LCPS obtained from BHK-TF cells transiently transfected with the two hybrid system with Gal4-Elk1 and gal4-luciferase.
Figure 4B:
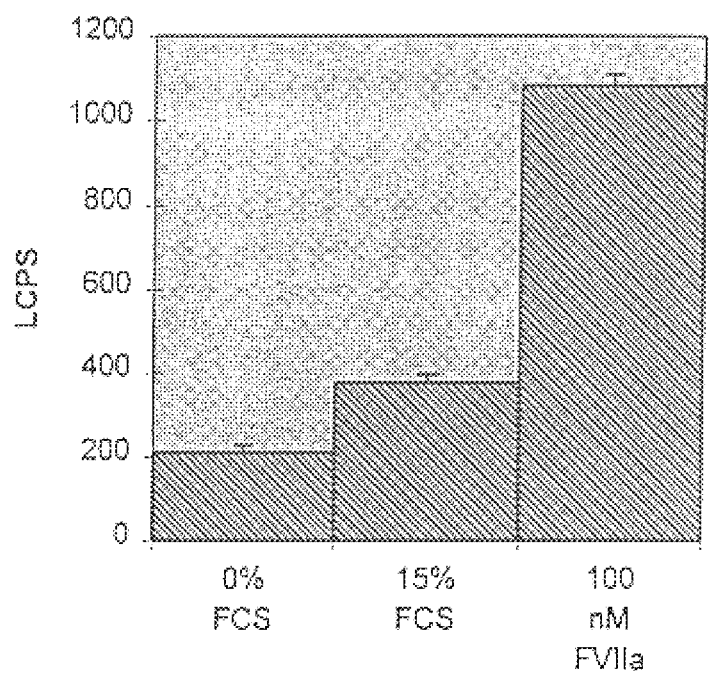

In this approach the specific activation of the Elk1 transcribtional factor is monitored. BHK cells stably transfected with TF were co-transfected with the following vectors pFR-luc (20 ug) (the reporter construct), pFA-Elk1 (0.5 µg) (the Gal4-Elk1 chimera expression vector), pFCdbd (14.4 µg) (carrier DNA) and pEGFP-N1 (3 µg) (reporter plasmid to monitor transfection efficiencies) (Clontech). pFRluc, pFA-Elk1 and pFCdbd are components of PathDetect system, Stratagene). A transfection efficiency of approximately 50% was estimated based on the number of cells expressing GFP (green fluorescent protein) (FIG. 4A). This mixture of transfected and non-transfected cells were stimulated with 100 nM FVIIa and assayed for luciferase expression. Cells stimulated with 100 nM FVIIa showed a luciferase expression 5.1 times higher than the background level with a standard deviation of 3–5% (FIG. 4B) demonstrating that Elk1 is activated upon binding of FVIIa to cell-surface TF.

Example 11
Monitoring the Signalling Pathway Induced Upon FVIIa—Tissue Factor Binding: The Antibody Approach.

In this set of experiments with TF transfected BHK, ECV-304 and MDCK cell lines two antibodies raised against the MAPK were used, one targeting activated as well as non-activated forms of MAPK, and another, targeting only the activated (phosphorylated) form of MAPK.

Figures 5A, 5B:
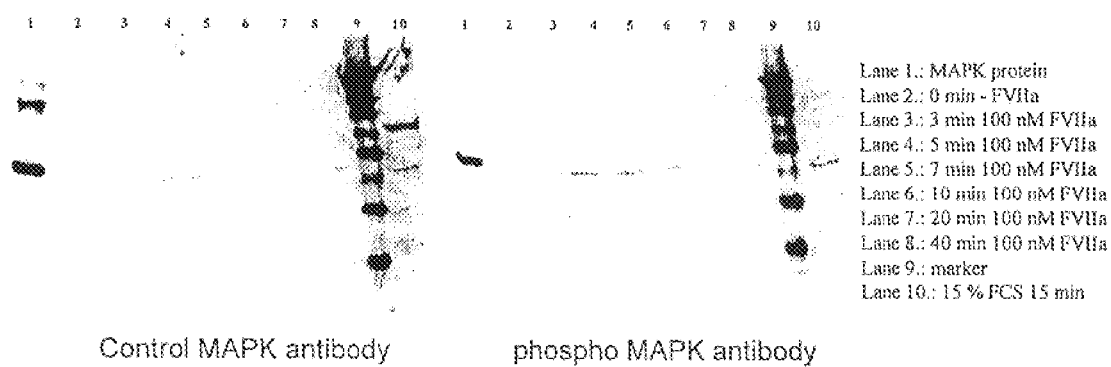
FIGS. 5A and 5B show the activation of MAPK p44/42: BHK TF 103 #11-2 cell line; Lane 3-8: Stimulation with 100 nM FVIIa for the time period indicated.

BHK cells stable transfected with human TF were grown to 90% confluence and starved in DMEM with 0. 1% FCS for 24 hours prior to stimulation with FVIIa. Samples for Western blotting were sampled at 0, 3, 5, 7, 10, 20 and 40 minutes after addition of 100 nM FVIIa. The result is shown in FIGS. 5A and B. The total amount of MAPK was essentially constant, whereas the antibody against the activated form of MAPK showed a temporally activation of MAPK p44/42 with a maximal activation at 3–7 minutes. Over the next 10 minutes the response declined to reach the background level at about 20 minutes after addition of FVIIa.

Figure 6A:
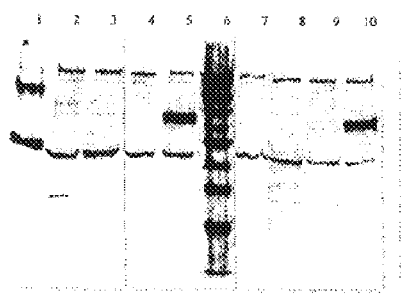
FIGS. 6A and 6B show the activation of MAPK p44/42: ECV-304 cell line (ATCC CRL-1998); IL-1β stimulated (Lane 2–5) and unstimulated (lane 7–9) cells exposed to 20 nM FVIIa for the time period indicated.
Figure 6B:
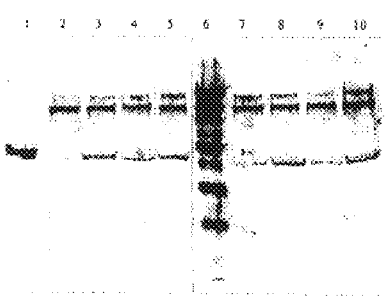

Immortalised human endothelial cells (ECV-304) were grown to 90% confluence and starved in medium 199 for 24 hours. In some experiments cells were exposed to IL-1β for five hours to further increase expression of cell surface TF prior to addition of FVIIa (FIGS. 6A and B).

Samples for Western blotting were taken at 0, 5 and 40 minutes after addition of 20 nM FVIIa to IL-1β stimulated and unstimulated cells. The total amount of MAPK was essentially constant thoughout the experiment whereas the activated form of MAPK showed a temporal activation with a maximal activation at 5 minutes on both stimulated and unstimulated cells.

Figures 7A, 7B:
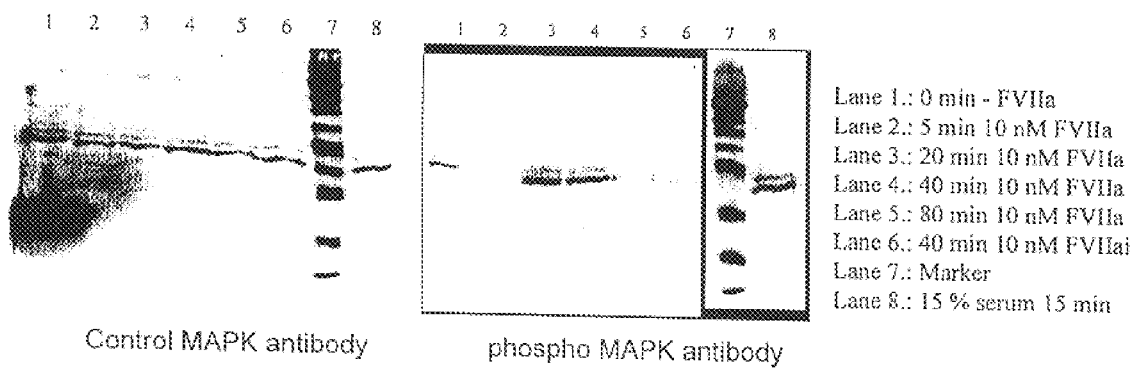
FIGS. 7A and 7B show the activation of MAPK p44/42: MDCK cell line (ATCC CCL-34) exposed to 10 nM FVIIa (Lane 1–5) and 10 nM FVIIai (Lane 6) for the time period indicated.

An epithelial Madin-Darby Canine Kidney (MDCK) cell line was grown to 100% confluence and starved in DMEM for 48 hours prior to assay. Samples for Western blotting were drawn at 0, 5, 20 40 and 80 minutes after addition of 10 nM FVIIa. An additional sample stimulated with 10 nM FVIIai was harvested after 40 minutes. Results shown in FIGS. 7A and B. The total amount of MAPK was essentially constant whereas the activated form of MAPK showed a temporal activation with maximal phosphorylation at 20 minutes with a gradual decline at 40 and 80 minutes. No significant phosphorylation of MAPK was observed with FVIIai after 40 minutes exposure.

These examples show that FVIIa is capable of inducing phosphorylation of MAPK/Erk1/2 in different TF expressing cell lines from various species. Furthermore FVIIai is not able to activate the same phosphorylation in MDCK cells.

Example 12
Experiments on Competition Between FVIIa and FVIIai.

Figure 8:
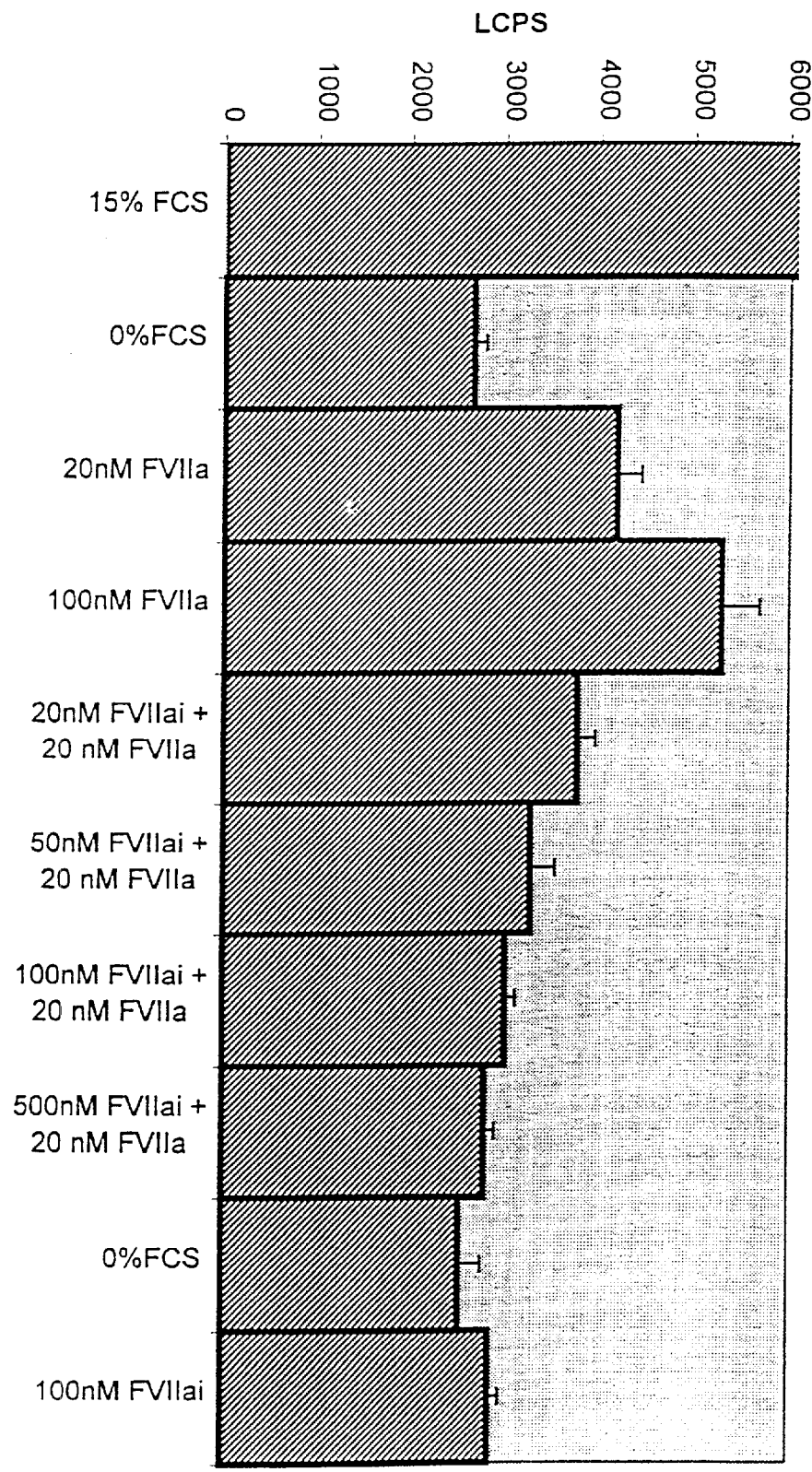
FIG. 8 illustrates the competition experiment between FVIIa and FVIIa in BHK-TF/KZ136 cells.

BHK cells stably transfected with the human TF and the reporter plasmid KZ136 were grown to 90% confluence, starved in DMEM with 0.1% FCS for 16 hours and then stimulated with FVIIa or FVIIai (FIG. 8). 100 nM FVIIai did not induce a serum response in contrast to 20 nM and 100 nM FVIIa which significantly increased the response. Also shown in FIG. 8 is an experiment where competition between FVIIa and FVIIai was studied. FVIIai was added to the cells 1 hour prior to stimulation with 20 nM FVIIa. The response induced by 20 nM FVIIa was inhibited 27%, 59%, 77%, and 91% by the addition of 20 nM, 50 nM, 100 nM, and 500 nM FVIIai, respectively. This showed that FVIIai could not induce signalling, and also that FVIIai could prevent FVIIa-induced signalling presumably by competing with FVII for a mutual binding site on TF.

Example 13
Characterisation of the Signalling Pathway Induced Upon Binding of FVIIa to Tissue Factor.

In this set of experiments with TF transfected BHK cell lines we used a phospho-specific antibody against phosphorylated (Thr202/Tyr204) p44/42 MAPK and an antibody targeting total p44/42 MAPK (New Englands Biolabs, Beverly, Mass.).

Figure 9A:
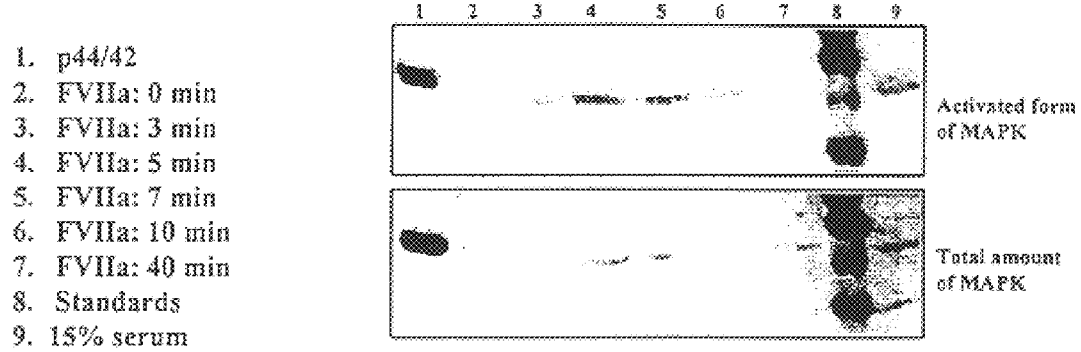
FIGS. 9A and 9B show the transient activation of MAPK p44/42.

BHK cells stable transfected with human TF were grown to 90% confluence and starved in DMEM with 0.1% FCS for 24 hours prior to stimulation. In FIG. 9A the cells were stimulated with 100 nM FVIIa for 0, 3, 5, 7, 10 and 40 minutes before the cells were lysed and samples for Western blotting were taken. The results in FIG. 9A (lower panel) show that the total amount of MAPK was essentially constant, whereas the results with the antibody against the activated form of MAPK (upper panel) showed a transient activation of MAPK p44/42 with a maximal activation at 3–7 minutes that declined over the next 40 minutes.

A similar experiment was performed with non-transfected BHK(-TF) cells. In these control cells the MAPK was not activated by FVIIa but a phosphorylated MAPK response was obtained with serum (results not shown).

Figure 9B:
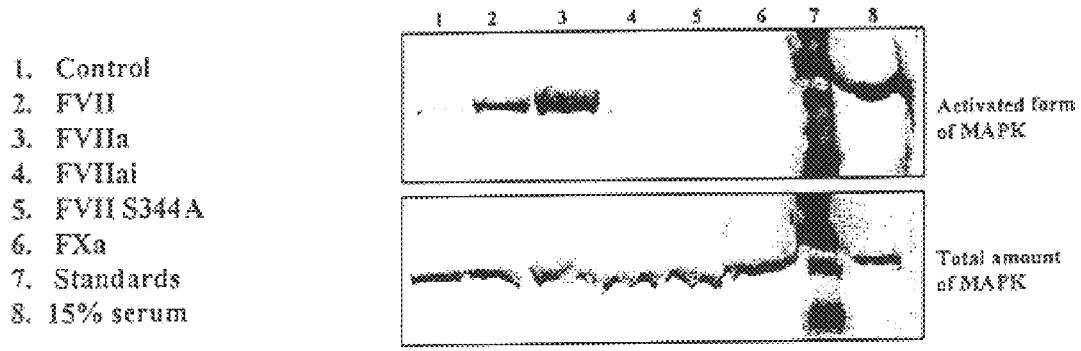

The results shown in FIG. 9B were obtained when BHK (+TF) cells were exposed to 100 nM FVII, FVIIa, FVIIai, [Ala344]FVII or FXa for 5 min. No effect on the total amount of p44/42 MAPK level was observed (lower panel) whereas a profound activation was seen with FVIIa, less so with FVII, and no significant activation was induced by FVIIai, [Ala344]FVII or FXa (upper panel). This strongly suggests that FVIIa activity was needed. Since FXa did not produce a significant increase in p44/42 phosphorylation, a putative FVIIa-mediated generation of FXa could not account for p44/42 MAPK activation with FVIIa. A brief EDTA wash supposed to remove possible trace amounts of vitamin K-dependent coagulation factors from the cell surface prior to FVIIa exposure was included in some experiments. This was without any reduction in MAPK phosphorylation, again supporting the notion that downstream coagulation reactions were not involved. In conclusion this example shows that FVIIa/TF induces a transient phosphorylation of the p44/42 MAPK and that the catalytic centre activity of FVIIa is required for this FVIIa-induced phosphorylation. Furthermore we conclude that an indirect signalling pathway involving FVIIa-mediated activation of FX is unlikely.

Example 14
The C-terminal Tail of Tissue Factor in Not Required for FVIIa-induced Signalling via the MAPK Pathway.

The cDNA coding for a truncated version of TF comprising the residues 1–247 was cloned into the mammalian Zem219b expression vector and transfected into BHK cells. This truncated TF without the C-terminal cytoplasmatic tail was expressed as a fully functional cofactor for FVIIa-mediated FX activation. We used the phospho-specific antibody against phosphorylated (Thr202/Tyr204) p44/42 MAPK and an antibody targeting total p44/42 MAPK (New Englands Biolabs, Beverly, Mass.) to monitor the phosphorylation of MAPK.

Figure 10:
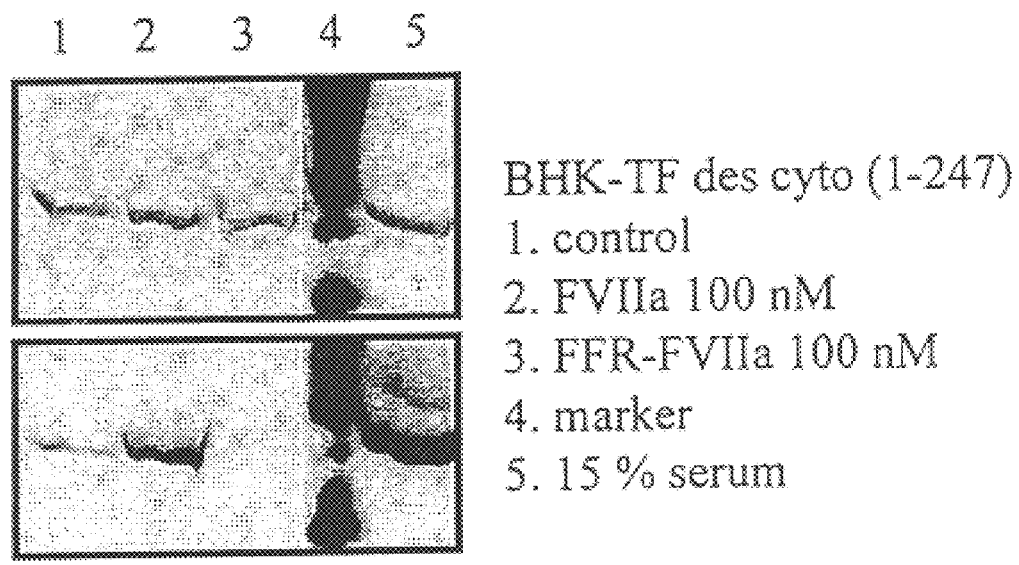
FIG. 10 shows FVIIa-induced signalling via the MAPK pathway using truncated TF (TF lacking the C-terminal end).

BHK cells stable transfected with human TF(1-247) were grown to 90% confluence and starved in DMEM with 0.1% FCS for 24 hours prior to stimulation. The cells were then stimulated with 100 nM FVIIa for 10 minutes before the cells were lysed and samples for Western blotting were taken. The results is shown in FIG. 10. The total amount of MAPK was essentially constant (upper panel), whereas the activated form of MAPK of MAPK p44/42 (lower panel) was phosphorylated as a result of exposure of the cells to FVIIa but not to FFR-FVIIa.

In conclusion this example demonstrates that FVIIa/TF-induced signal transduction via the MAPK pathway takes place independent of the presence of the cytoplasmatic tail of TF.

Example 15
Regulation of Chemotaxis by FVIIa-induced Signalling

The following experiments were performed to determine the effect of FVIIa-induced signalling on cell migration.

A. Methods

Cell cultures. Human foreskin fibroblasts AG1518 and AG1523 were grown to confluence in Eagle's MEM supplemented with 10% fetal bovine serum (FBS). Before use, the cells were detached by trypsinization (2.5 mg/ml for 10 min at 37° C.), washed in Hank's balanced salt solution, and resuspended in Eagle's MEM with 10% FBS or in Ham's medium supplemented with 0.1% FBS.

Proteins. Human FVIIa (Novo Nordisk A/S, Gentofte, Denmark), was expressed and purified as described (Thim et al., *Biochemistry* 27, 7785–7793 (1988)). FFR-FVIIa (Novo Nordisk) was obtained by blocking of FVIIa in the active site with D-Phe-L-Phe-L-Arg chloromethyl ketone (Sorensen et al., *J. Biol. Chem.* 272, 11863–11868 (1997)). Hirudin was purchased from Sigma. LY294002, U73122 and U73343 were obtained from Biomol (Plymouth Meeting, Pa.). Anti-TF monoclonal antibodies, TF8–5G9, TF9–5B7 and MTFH-1 were as described (Morrissey, et al., *Thromb. Res.* 52, 247–261 (1988)).

Flow cytometry. The surface expression of TF was analysed by immunofluorescence with a flow cytometer (Coulter Epics XL-MCL, Beckman Coulter, Fullerton, Calif., Coulter Electronics, USA). The instrument was calibrated daily with Immuno-Check™ or Flow Check™ calibration beads (Coulter). For indirect immunofluorescence experiments, AG1518 or AG1523 fibroblasts were washed twice with PBS containing 0.1% bovine serum albumin (BSA), incubated for 30 min on ice with a fluorescein-isothiocyanate (FITC)-labelled anti-human TF monoclonal antibody (4508CJ, American Diagnostica, Greenwich, Conn. USA). The anti-*Aspergillus niger* glucose oxidase monoclonal IgG1 (Dakopatts) was used as a negative control. Mean channel fluorescence intensity (MFI) and percentage of positive cells were determined for each sample.

Determination of TF activity. The procoagulant activity of TF was determined as described (Lindmark, et al., *Br. J. Haematol.* 102, 597–604 (1998)). Briefly, aliquots containing $0.2 \times 10^5$ AG1518 or AG1523 fibroblasts were washed twice with PBS and placed in the wells of a 96-well microtitreplate (Nunc, Roskilde, Denmark). The procoagulant activity was measured in a two-stage amidolytic assay in which a chromogenic substrate, S-2222 (Chromogenix, Mölndal, Sweden), is cleaved by FXa, which in turn is activated from FX by the TF/FVIIa complex. A reaction mixture containing final concentrations of 0.6 mM S-2222, 2 mM $CaCl_2$ and coagulation factors from the factor concentrate Prothromplex-T™ TIM4 (Baxter, Vienna, Austria) at a final concentration of 1 U/ml FVII and 1.2 U/ml FX, was added to the wells, and change in absorbance at 405 nm following a 30 minutes incubation at 37° C. was determined. The measurements were done in triplicate.

Chemotaxis assay. The migration response of fibroblasts was assayed by means of the leading front technique in a modified Boyden chamber, as previously described (Nister et al., *Cell* 52, 791–799 (1988); Siegbahn et al. *J. Clin. Invest.* 85, 916–920 (1990)). Micropore filters (pore size 8 μm) were coated with a solution of type-i collagen at room temperature over night. The filters were air dried for 30 minutes immediately before use.

Human foreskin fibroblasts AG1523 were grown to confluence in Eagle's MEM supplemented with 10% FBS. The cells were detached by trypsinization (2.5 mg/ml for 10 minutes at 37° C.) and suspended in Eagle's MEM with 10% FBS. The fibroblasts were incubated for 10 minutes with or without FVIIa or FFR-FVIIa before assay. One hundred microliters of the cell suspension ($2 \times 10^5$ cells/ml) was added above the filter of the Boyden chamber. PDGF-BB was diluted in assay media (Eagle's MEM with 10% FBS) and added below the filter in the chamber. The cells were incubated for 6 hours at 37° C. in a humidified chamber containing 95% air/5% $CO_2$. FVIIa or FFR-FVIIa were present during the entire experiment. The filters were then removed, fixed in ethanol, stained with Mayer's Hemalun, and mounted. Migration was measured as the distance of the two furthest migrating fibroblast nuclei of one high-power field (12.5×24) in focus. The migration distance in each filter was calculated as the mean of the readings of at least three different parts of the filter. Experiments were performed with two to four separate filters for each concentration of chemoattractant. For each set of experiments, the migration of fibroblasts toward the assay media served as control. In cases when anti-TF monoclonal antibodies or inhibitors to coagulation factors, TAP and Hirudin, were used, cells were preincubated for 10 minutes with these agents, then with or without FVIIa or FFR-FVIIa before the chemotaxis assay was performed. Antibodies, TAP or Hirudin were also present during the entire chemotaxis experiment. In experiments where the effects on the migration response of different inhibitors, LY294002, U73122 or U73343, were tested, cells were preincubated for 30 minutes with the inhibitors at indicated concentrations, and the inhibitors were also present throughout the experiments.

Assay for release of inositol trisphosphate ($IP_3$). Six-well plates with semi-confluent cultures of AG1518 human fibroblasts, were incubated over night (approx. 20 hours) with 2 μCi of myo($^3$H) inositol (Amersham) in 2 ml Ham's F12 with 0.1% FBS. Medium was changed to Ham's F12 with 0.1% FBS (containing 2 mM $CaCl_2$) and 20 mM LiCl and the cells were incubated for 15 minutes at 37° C. Cells were then incubated in the absence or presence of 100 nM FVIIa or 100 nM FFR-FVIIa for one hour. PDGF-BB (0, 10 or 100 30 ng/ml) was added, and the incubation was continued for 10 minutes at 37° C. The $IP_3$ assay was performed asdescribed (Eriksson et al., *J. Biol. Chem.* 270, 7773–7781 (1995)).

Assay for agonist-induced PLC-γ1 phosphorylation. Semi-confluent cultures of AG1518 were serum starved overnight (approx. 20 hours) in medium containing 0.1% FBS, and then incubated in the absence or presence of 100 nM FVIIa or FFR-FVIIa for one hour followed by incubation with 0, 2, 10 or 100 ng/ml PDGF-BB for 5 minutes at 37° C. Cells were lysed and PLC-γ1 was precipitated, essentially as described (Hansen et al., *EMBO J.* 15, 5299–5313 (1996) with anti-PLC-γ1 antiserum generated by immunizing rabbits with a peptide corresponding to the carboxyterminus of bovine PLC-γ1 (Artega et al., *Proc. Natl. Acad. Sci. USA* 88, 10435–10439 (1991)). Samples were separated by SDS-PAGE and immunoblotted with the phophotyrosine antibody PY99.

Statistical analysis. Data were analysed using the Statistica TM for Windows package (StatSoft, Tulsa, Okla. USA). A Student's t-test for dependent samples was used to determine statistical significance between different data sets. P values of <0.05 were considered statistically significant.

Figure 11A:
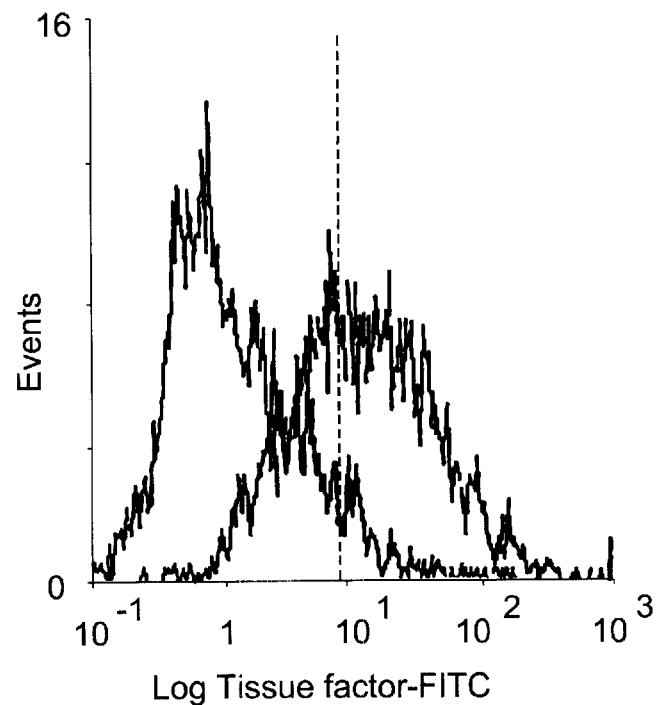
FIG. 11A is a graphic illustration of flow cytometric analysis of TF expression in fibroblasts. The cells were stained with either a murine monoclonal fluoresceinisothiocyanate (FITC)-conjugated mouse anti IgG-antibody (unfilled area) that was used as negative control or a monoclonal FITC-conjugated anti-tissue factor (TF) antibody (filled area).
Figure 11B:
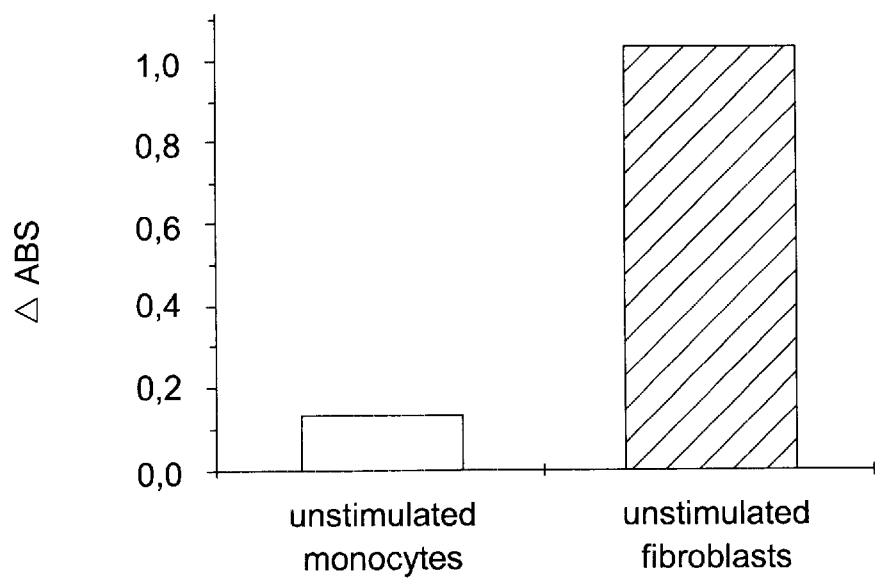
FIG. 11B is a graphic illustration of the procoagulant activity of fibroblasts.

B. RESULTS:
Effects of FVIIa and FFR-FVIIa on the Chemotactic Response of Fibroblasts to Platelet-Derived Growth Factor (PDGF) BB Fibroblasts expressing active TF (FIG. 11) were incubated with 100 nM of FVIIa and seeded in the upper part of the modified Boyden chamber; while media containing 10% FBS and PDGF-BB at different concentrations were added below the 150 μm micropore filter. The migration of the cells under conditions where medium containing 10% FBS without PDGF-BB was added below the filter was used as a measure of random migration, and calculated as 100% migration.

Figure 12:
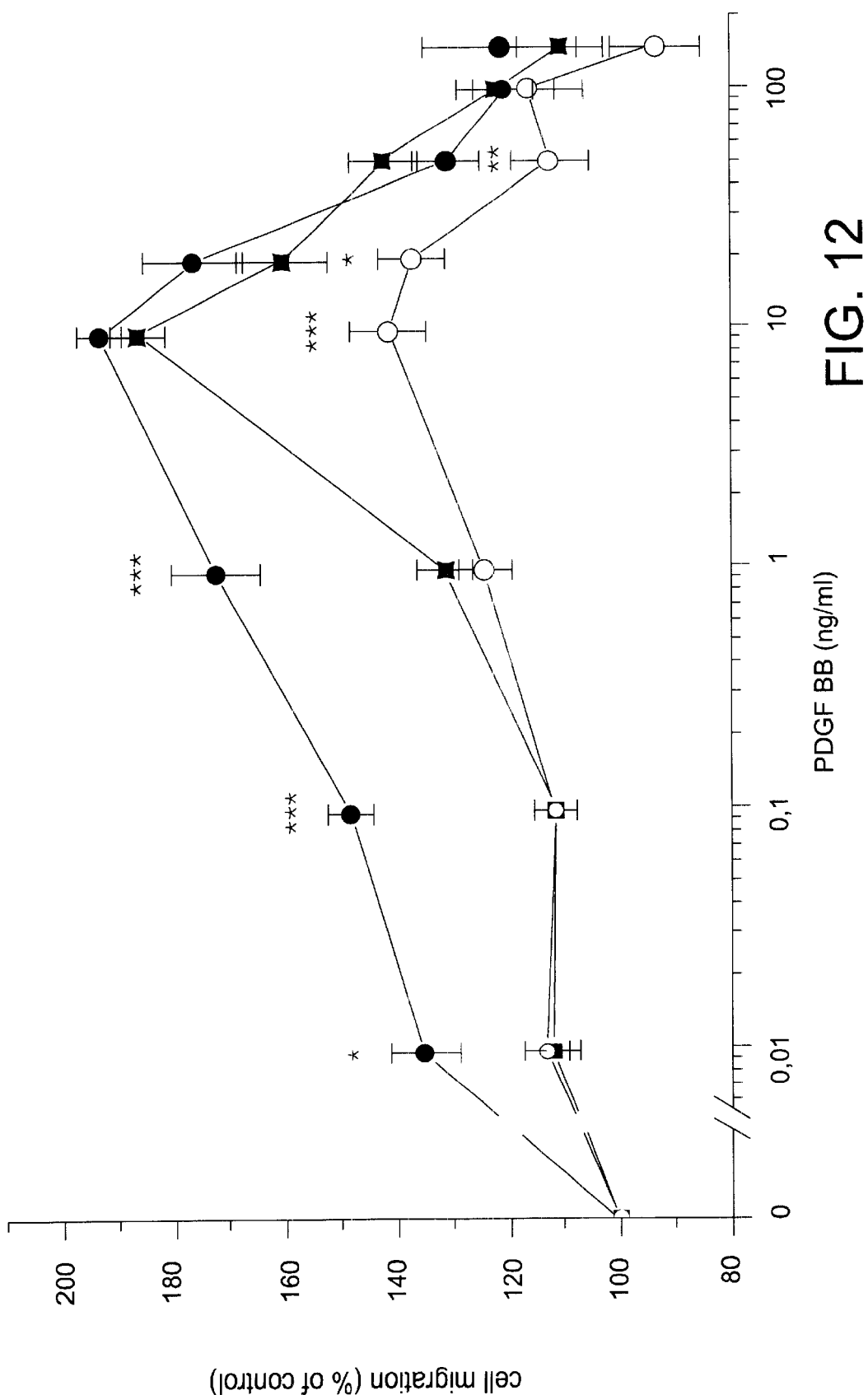
FIG. 12 is a graphic illustration of the effects of FVIIa and FFR-FVIIa on Platelet-Derived Grout Factor (PDGF)-BB induced chemotaxis in human fibroblasts.

A significant migration response was recorded at a concentration of 0.01 ng/ml PDGF-BB in cells stimulated by FVIIa compared to 1 ng/ml PDGF-BB for cells not ligated with FVIIa, i.e. a 100-fold difference in concentration (FIG. 12). At 0.01–0.1 ng/ml PDGF-BB, the migration response to FVIIa increased in a dose dependent manner starting at 25 nM, with a maximal effect at 50–100 nM FVIIa (FIGS. 13A–D). No enhancement of random migration was observed after activation with FVIIa. To test whether the proteolytically active FVIIa was mandatory for the hyperchemotactic response to PDGF-BB, fibroblasts were also incubated with 100 nM FFR-FVIIa and assayed in the Boyden chamber in the same way (FIG. 12). No increased chemotaxis was observed with FFR-FVIIa at low concentrations of PDGF-BB, 0.01–1 ng/ml. In contrast, a pronounced suppression of chemotaxis induced by 10–50 ng/ml PDGF-BB was achieved by 100 nM FFR-FVIIa (FIGS. 12 and 13A–D).

Figure 14:
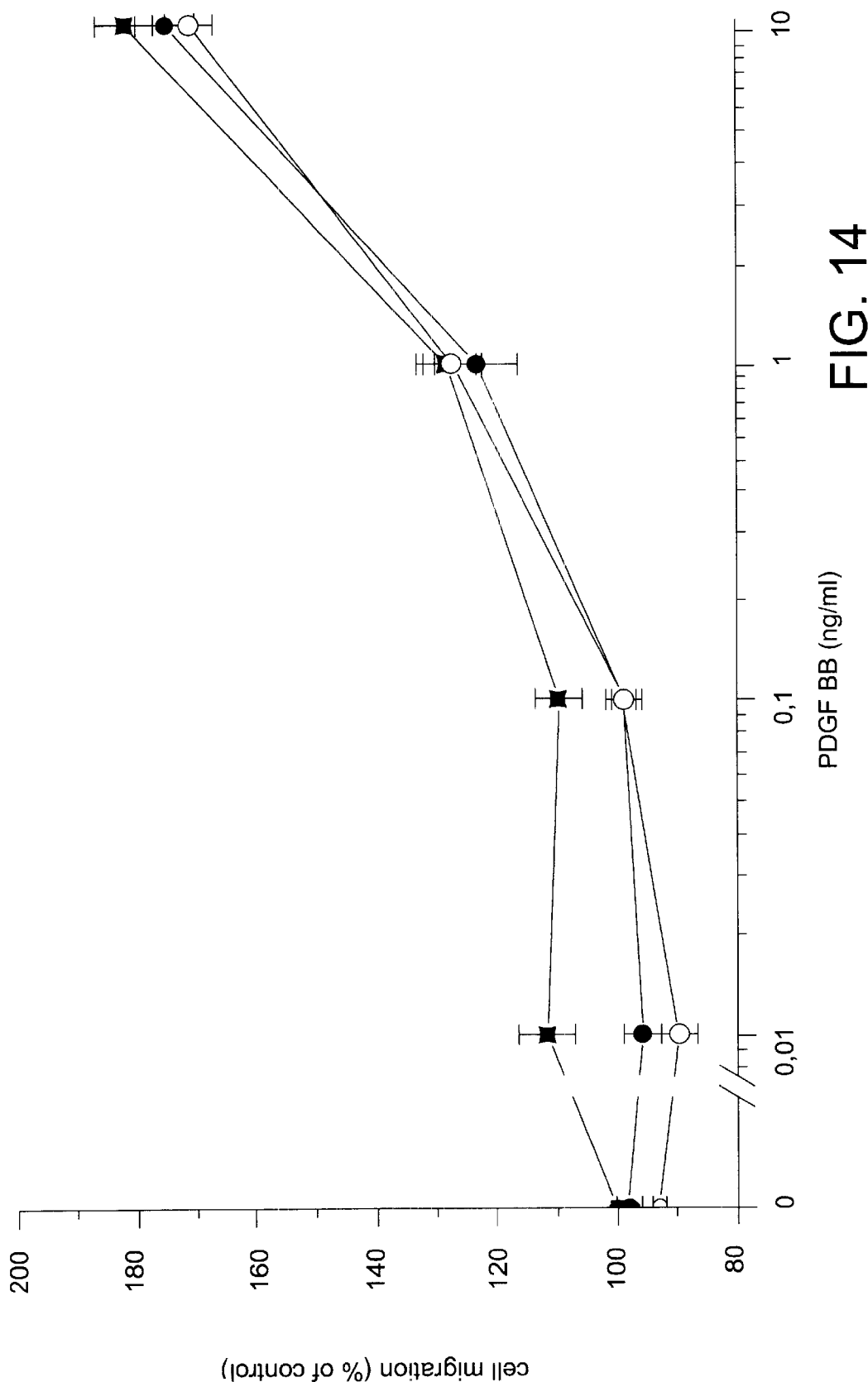
FIG. 14 is graphic illustration of the effect of a mixture of three monoclonal antibodies to TF on the effects of FVIIa and FFR-FVIIa on PDGF-BB induced chemotaxis in fibroblasts.

When fibroblasts were preincubated with a mixture of three different TF antibodies and then with FVIIa or FFR-FVIIa, the migration response to PDGF-BB was identical to the response of fibroblasts without the presence of ligand bonded to TF (FIG. 14). An irrelevant monoclonal IgG antibody did not prevent either hyperchemotaxis induced by FVIIa nor inhibition of the migration response induced by FFR-FVIIa. The presence of the IgG antibodies or the three TF antibodies did not change random migration of the fibroblasts.

The Hyperchemotactic Response is not Mediated by FXa or by Thrombin

Figure 15A:
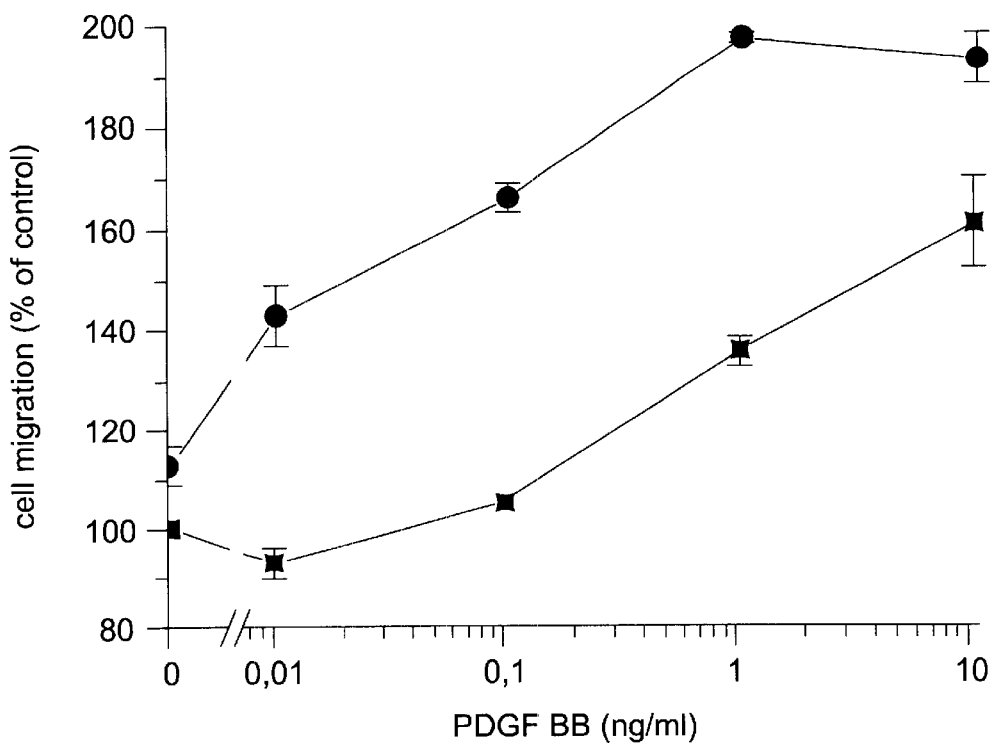
FIGS. 15A and 15B are graphic illustrations of the influence of FXa on the chemotactic response to PDGF-BB induced by FVIIa in fibroblasts preincubated with 200 nM TAP (FIG. 15A) or with 0.2–2 μM TAP (FIG. 15B) and then with 100 nM FVIIa. TAP was present during the entire experiments.
Figure 15B:
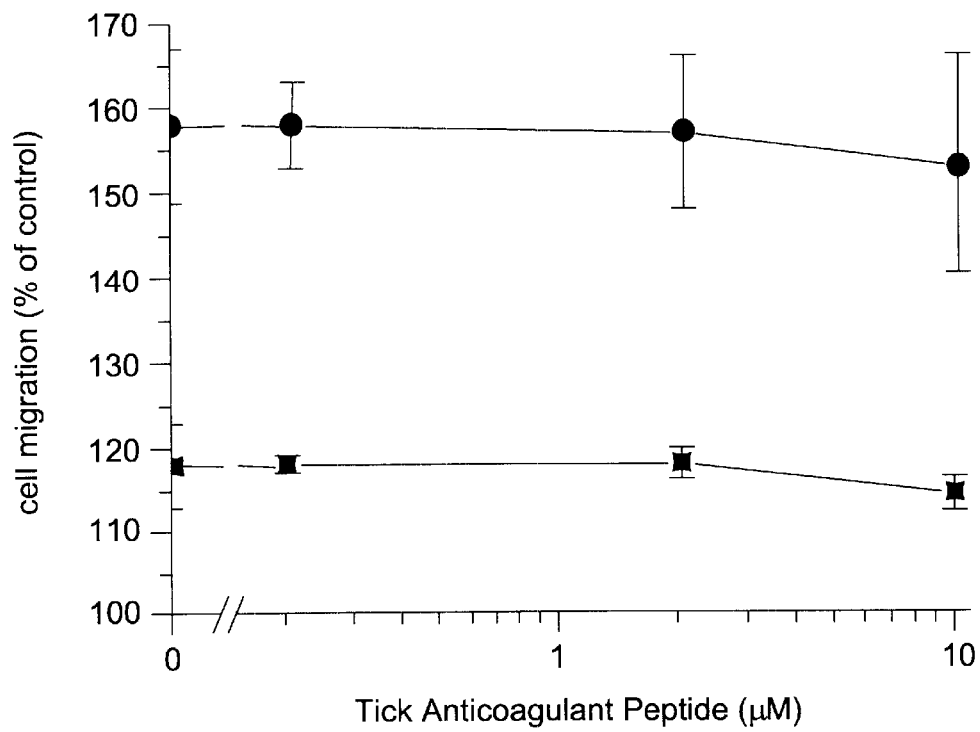
Figure 16:
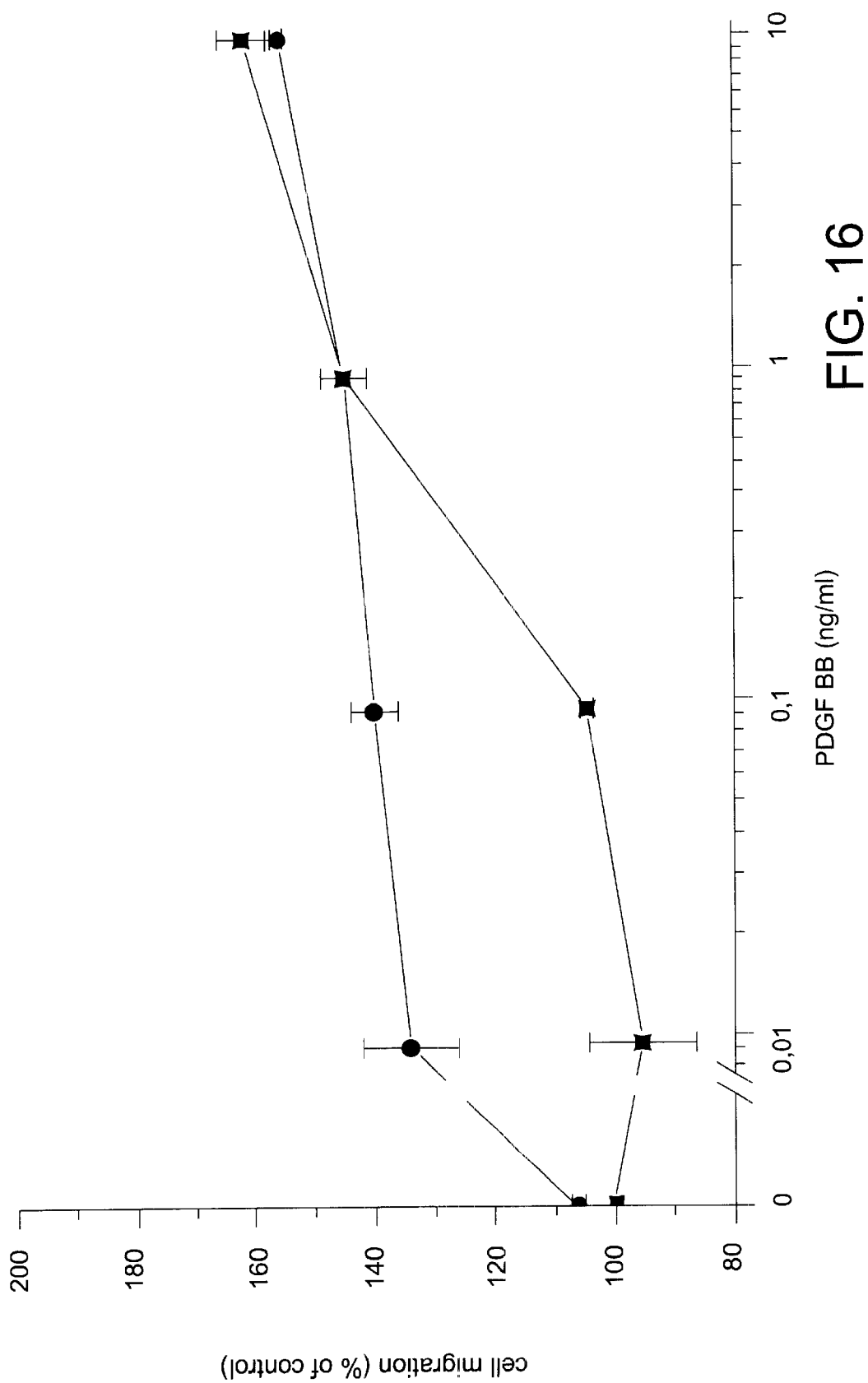
FIG. 16 is a graphic illustration of the influence of thrombin on the chemotactic response to PDGF-BB induced by FVIIa. Fibroblasts were preincubated with 5 U/mL (final concentration) Hirudin and then with 100 nM FVIIa.

Since FVIIa-induced signal transduction leading to the hyperchemotactic response to PDGF-BB was dependent on the catalytic activity of FVIIa, it was important to determine whether signalling occurred directly or via FXa or thrombin generated by the FVIIa/TF complex. The enhanced migration response transduced by FVIIa/TF was not blocked by 0.2–10 $\mu$M Tick anticoagulant peptide (TAP), which specifically blocks the active site of FXa and prevents a further activation of the coagulation cascade leading to thrombin formation (FIGS. 15A,B). Addition of 5 U/ml Hirudin, a specific thrombin inhibitor, had no any effect on FVIIa/TF induced hyperchemotaxis (FIG. 16). TAP and Hirudin did not influence the migration of fibroblast in response to PDGF without the presence of the ligand FVIIa (FIGS. 15, 16). Thus, it is unlikely that the effect of FVIIa on chemotaxis is mediated via the activation of FX or thrombin.

The Hyperchemotactic Response to PDGF-BB is Influenced by PLC-dependent Pathways, but is Independent of PI13'-kinase.

Figure 17:
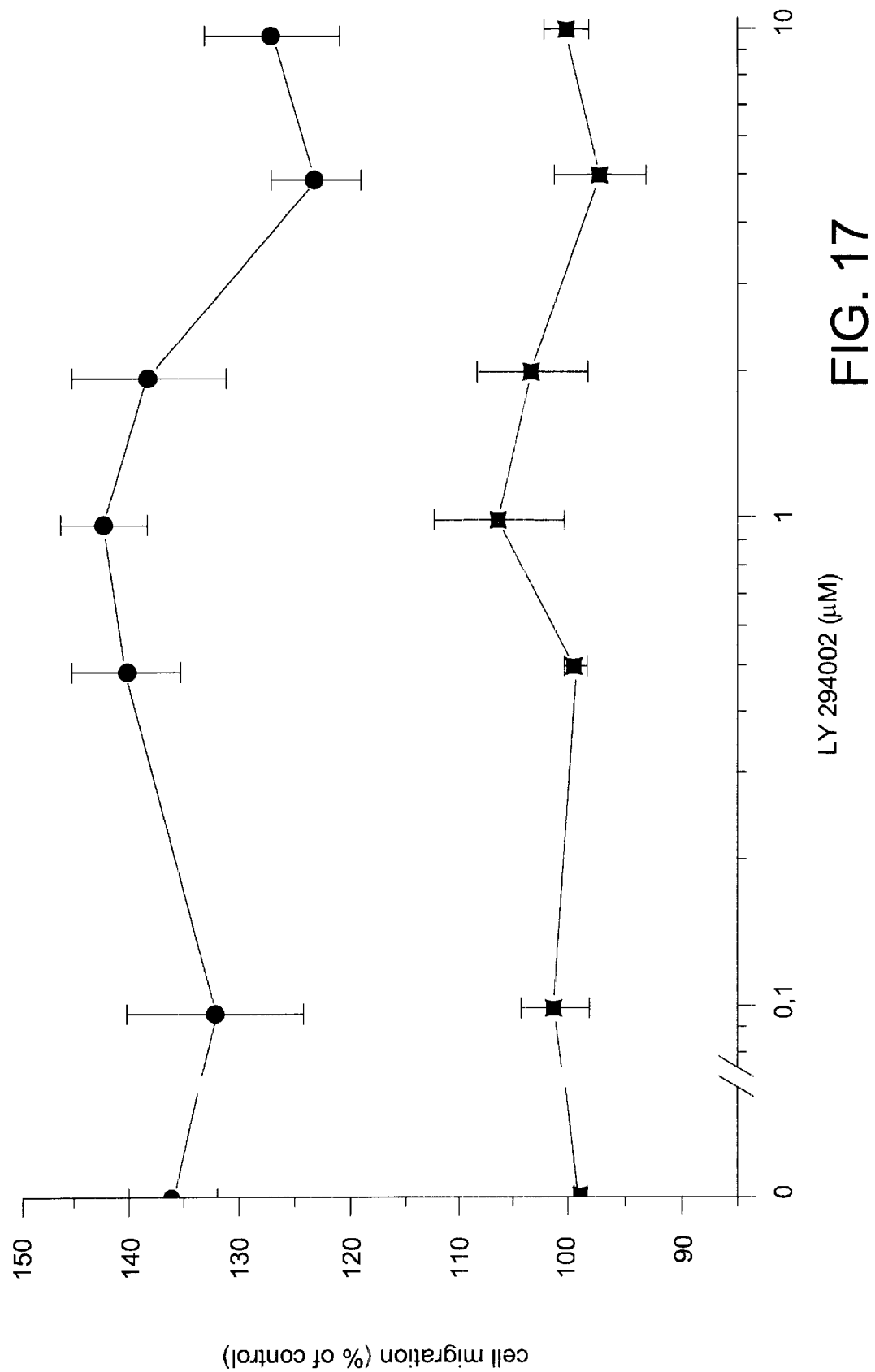
FIG. 17 is a graphic illustration of the effect of inhibition of PI3'-kinase on chemotaxis in fibroblasts incubated with FVIIa. Cells were preincubated with varying concentrations of LY294002 for 30 min at 37° C., and then with 100 nM FVIIa or without FVIIa.

Activation of PI3' kinase has recently been shown to be important for PDGF $\beta$-receptor induced chemotaxis (Wennstrom et al., *Oncogene* 9, 651–660 (1994); Hansen et al.,. *EMBO J.* 15, 5299–5313 (1996).) Therefore, we investigated whether LY294002, a specific PI3'-kinase inhibitor, was able to block the chemotactic response induced by FVIIa/TF signalling. Fibroblasts were pretreated with LY294002 at indicated concentrations for 30 minutes at 37° C. before the addition of 100 nM FVIIa and assayed in the Boyden chamber as described. The concentration of PDGF-BB was kept constant at 0.1 ng/ml throughout the assay, i.e. a very low concentration at which FVIIa/TF induced a significant chemotactic response. LY294002 was present during the entire experiments. FIG. 17 shows that the migration response to PDGF-BB mediated by FVIIa/TF-signalling was unaffected by the inhibition of PI3'-kinase.

Figure 18A:
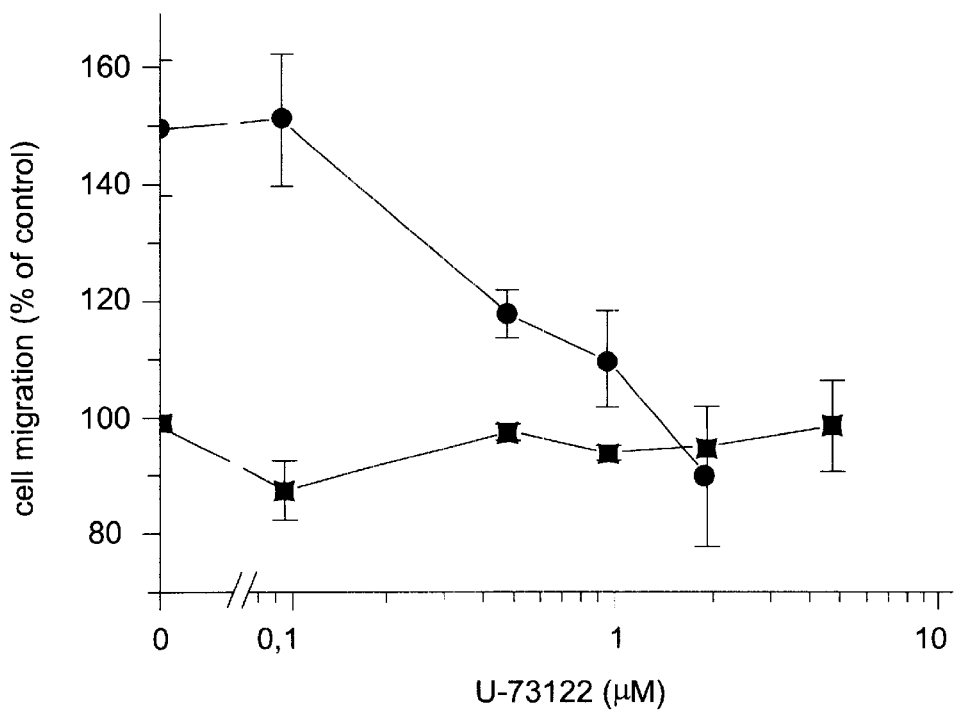
FIGS. 18A and 18B are graphic illustrations of the effect of inhibition of PLC on chemotaxis in fibroblasts incubated with FVIIa. Cells were incubated with varying concentrations of U73122 (active PLC inhibitor) (A) or U73343 (inactive control) (B) for 30 min at 37° C. before incubation with or without 100 nM FVIIa, and then assayed in the Boyden chamber to a concentration gradient of 0.1 ng/mL PDGF-BB.
Figure 18B:
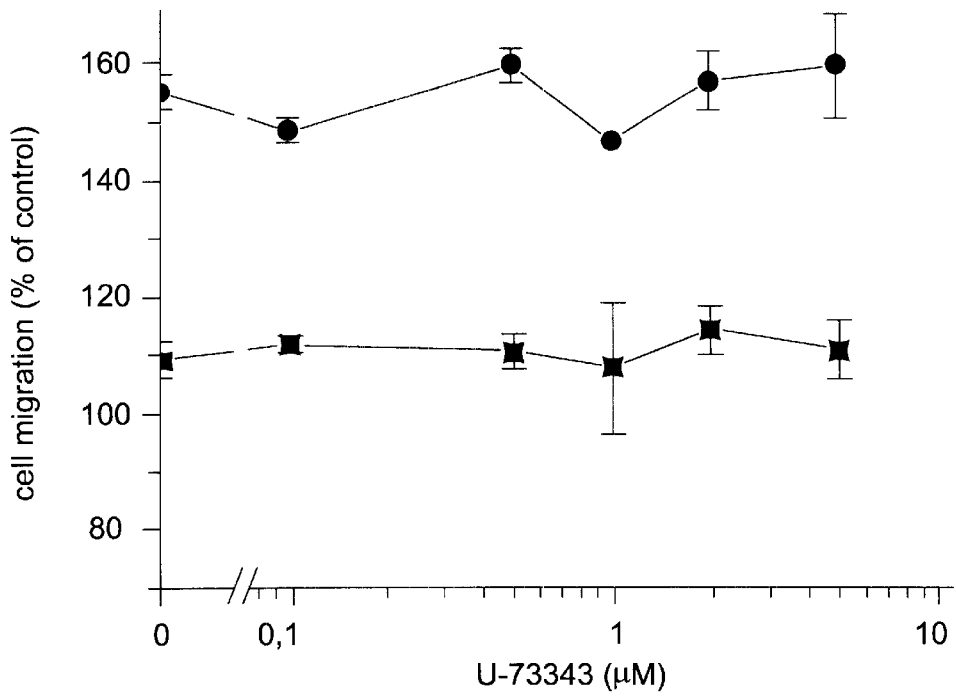

To investigate whether the FVIIa/TF-induced chemotactic response involved the activation of phosphatidylinositol specific phospholipase C (PLC), we preincubated the fibroblasts with different concentrations of U73122, a specific PLC-inhibitor, for 30 minutes at 37° C. before adding 100 nM FVIIa; the cells were then subjected to the chemotaxis assay in the presence of the inhibitor. A close analogue, U73343, without effects on PLC was used as negative control. The concentration of PDGF-BB was kept constant at 0.1 ng/ml also in these experiments. Pretreatment of the cells with the active PLC-inhibitor U73122 inhibited the hyperchemotacic response to 0.1 ng/ml PDGF-BB in a dose-dependent way, with a total inhibition at 1 $\mu$M (FIG. 18). No effect on chemotaxis was observed when the inactive analogue U73343 was used.

FVIIa/TF Induce Activation of PLC

Figure 19:
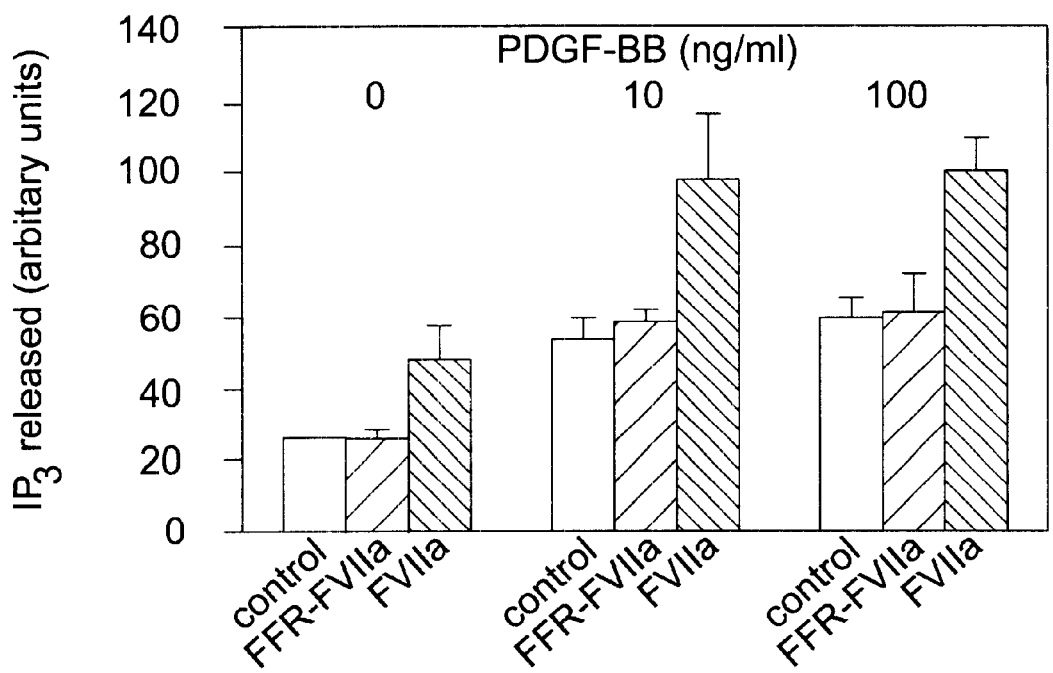
FIG. 19 is a graphic illustration of the release of inositol trisphosphate ($IP_3$) from fibroblasts stimulated with FVIIa, FFR-FVIIa alone or in combination with PDGF-BB. Open bars show cells without FVIIa or FFR-FVIIa (control), hatched bars show cells with FFR-FVIIa, and black bars show cells incubated with FVIIa.

To further explore the importance of PLC activity for the hyperchemotactic response, we also analysed the direct effects of FVIIa/TF on PLC activity in fibroblasts. Activation of PLC leads to production of two second messengers, inositol-1,4,5-trisphosphate ($IP_3$) and diacylglycerol. Fibroblasts were incubated with myo [$^3$H] inositol overnight, and then with 100 nM FVIIa or FFR-FVIIa for 60 minutes, followed by incubation with or without PDGF-BB at indicated concentrations. Treatment with 100 nM FVIIa alone for 60 minutes induced $IP_3$ release in fibroblasts at the same level as 10 ng/ml and 100 ng/ml PDGF-BB alone did (FIG. 19). Moreover, the combination of 100 nM FVIIa and 10 ng/ml or 100 ng/ml PDGF-BB doubled the $IP_3$ release. The active site-inhibited FVIIa did not induce release of $IP_3$. These results clearly show that PLC is activated upon binding of FVIIa to TF.

Figure 20:
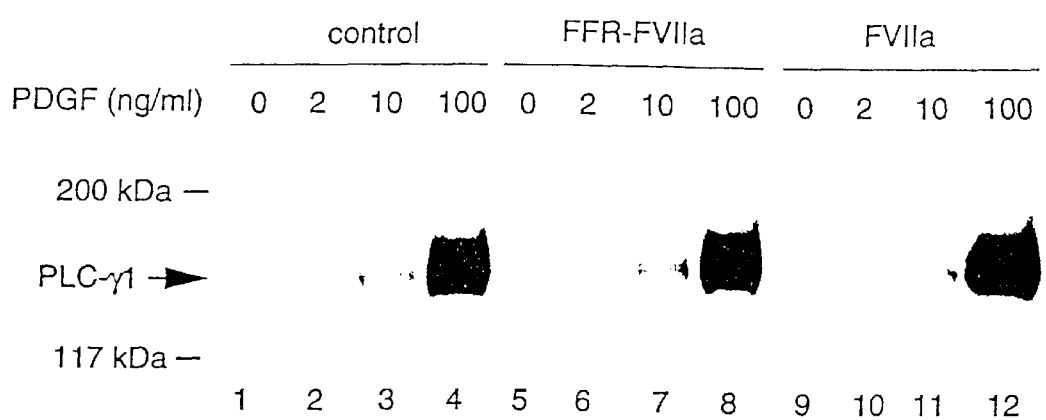
FIG. 20 is a photographic illustration of tyrosine phosphorylation of PLC-γ1 in response to PDGF-BB alone (control), FVIIa or FFR-FVIIa in combination with PDGF-BB. Cells were incubated with 100 nM FVIIa or FFR-FVIIa for one hour, and then with or without PDGF-BB at indicated concentrations. Cell were lysed and tyrosine phosphorylation of PLC-γ1 detected.

Phosphorylation of PLC-$\gamma$1 is not Enhanced by TF/FVIIa Signalling in Fibroblasts In order to determine whether the PLC-$\gamma$1 isoform, which is activated by certain tyrosine kinase receptors, was responsible for the increased PLC activity induced by FVIIa/TF, tyrosine phosphorylation of PLC-$\gamma$1 was studied. Fibroblasts were incubated in the absence or presence of 100 nM FVIIa or FFR-FVIIa for one hour, followed by the stimulation with 0, 2, 10 or 100 ng/ml PDGF-BB. After 5 minutes of incubation, the cells were lysed and PLC-$\gamma$1 was immunoprecipitated, separated by SDS-PAGE and immunoblotted with antiphosphotyrosine antibodies. Whereas a significant increase in tyrosine phosphorylation of PLC-$\gamma$1 was recorded with increasing concentrations of PDGF-BB, addition of FVIIa alone to the fibroblasts did not induce any tyrosine phosphorylation of PLC-$\gamma$1 (FIG. 20). Moreover, the combination of FVIIa and PDGF-BB at different concentrations did not induce any further phosphorylation compared to stimulation with PDGF-BB alone (FIG. 20). FFR-FVIIa had no effect on PLC-$\gamma$1 tyrosine phosphorylation (FIG. 20). Thus, other PLC isoforms than PLC-$\gamma$1 are responsible for the increased PLC activity after FVIIa stimulation.

C. DISCUSSION

These experiments demonstrated that human fibroblasts with a constitutive expression of TF upon ligand binding of FVIIa migrate towards extremely low concentrations of PDGF-BB. TF/FVIIa alone did not induce enhanced spontaneous migration, i.e. random migration. Thus, a combination of intracellular signal transduction by FVIIa/TF and the growth factor PDGF-BB was necessary to achieve the motility response. Not only binding to TF, but also the catalytic activity of TF/FVIIa was mandatory, since active-site inhibited FVIIa did not elicit enhanced migration response. Furthermore, inhibitory monoclonal antibodies prevented enhancement of the chemotactic response by FVIIa. We also excluded that indirect signalling occured due to FXa or thrombin, since TAP and Hirudin had no effect on FVIIa/TF induced chemotaxis. We instead found that increasing concentrations of FFR-FVIIa actively inhibited PDGF-BB induced chemotaxis. Fibroblasts incubated with FFR-FVIIa showed completely normal random migration. The inhibitory effect of FFR-FVIIa on PDGF-BB-induced chemotaxis was not observed in the presence of the combination of anti-TF antibodies thereby ruling out the possibility of FFR-FVIIa being toxic. The results suggest rather, that in cells expressing PDGF P-receptors and TF, the FVIIa/TF complex is of importance for the chemotactic response to PDGF-BB. Taken together, our data strongly support the idea that cell migration is one important morphogenic function induced by FVIIa/TF signalling. A cellular migration response is probably mediated in cooperation with different chemotactic factors.

Chemotaxis plays a pivotal role in wound healing, angiogenesis and metastasis. Chemotaxis is also an important component in the development of atherosclerotic plaques. In these processes a variety of cells express TF as well as PDGF and PDGF receptors. Restenosis is a major complication following interventional procedure of obstructed arteries. PDGF has been implicated in the vessel wall's response (neointima formation) to mechanical injury by mediating the migration and proliferation of smooth muscle cells and fibroblasts. We have shown now for the first time that FVIIa binding to TF-expressing cells have an increased chemotactic response to PDGF which is independent of the coagulation.

What is claimed is:

1. A method for modifying cell motility, said method comprising contacting a cell that expresses tissue factor (TF) on its surface with a motility modifying-effective amount of a compound selected from the group consisting of Factor VIIa and a Factor VIIa agonist, under conditions that result in modification of the motility of said cell.

2. A method as defined in claim 1, wherein said TF-expressing cell is selected from the group consisting of fibroblasts, monocytes, macrophages, smooth muscle cells, endothelial cells, and tumor cells.

* * * * *